(12) United States Patent
Wyrick

(10) Patent No.: US 8,187,224 B2
(45) Date of Patent: *May 29, 2012

(54) METHODS PERFORMED BY MEDICINE INJECTION APPARATUSES

(75) Inventor: Ronald E. Wyrick, Spokane, WA (US)

(73) Assignee: Washington Biotech Corporation, Spokane, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/569,737

(22) Filed: Sep. 29, 2009

(65) Prior Publication Data

US 2010/0094217 A1 Apr. 15, 2010

Related U.S. Application Data

(60) Continuation of application No. 11/982,397, filed on Oct. 31, 2007, now Pat. No. 7,931,618, which is a division of application No. 11/006,382, filed on Dec. 6, 2004, now Pat. No. 7,297,136.

(51) Int. Cl.
*A61M 5/00* (2006.01)

(52) U.S. Cl. .................................................. 604/117

(58) Field of Classification Search ............... 604/181, 604/187, 191, 117, 135, 136, 134, 138, 139, 604/110, 121, 157, 255, 197, 200, 201, 218, 604/232

See application file for complete search history.

(56) References Cited

U.S. PATENT DOCUMENTS

| | | |
|---|---|---|
| 1,718,701 A | 6/1929 | O'Sullivan |
| 2,168,686 A | 8/1939 | Saffir |
| 3,055,362 A | 9/1962 | Uytenbogaart |
| 3,252,446 A | 5/1966 | Bateman |
| 3,572,336 A * | 3/1971 | Hershberg .................. 604/136 |
| 3,605,742 A * | 9/1971 | Tibbs ........................... 604/112 |
| 3,605,744 A | 9/1971 | Dwyer |
| 3,882,863 A | 5/1975 | Sarnoff et al. |
| 3,910,444 A | 10/1975 | Foster |

(Continued)

FOREIGN PATENT DOCUMENTS

EP 1958654 8/2008

(Continued)

OTHER PUBLICATIONS

AAAAI. "Position Statement: Anaphylaxis in Schools and Other Child-Care Settings," http://www.aaaai.org/media/resources/academy_statements/position_statements/ps34.asp Jun. 23, 2003, pp. 1-6.

(Continued)

*Primary Examiner* — Jackie Ho
*Assistant Examiner* — Laura Schell
(74) *Attorney, Agent, or Firm* — Wells St. John P.S.

(57) ABSTRACT

Operations performed by a medicine injector having a barrel with a receiving cavity to slidably receive a syringe subassembly for axial movement therein. Upon removal of a safety and release of a syringe driver, the syringe driver moves forward and injects the syringe needle. One or more penetration controls are shown for controlling injection needle penetration depth. In some forms of penetration control a sleeve and spring are used in the methods performed. This construction and a cushioning piece or pieces may be used to reduce the forces experienced by the syringe subassembly. A load distribution ring may further be used with a cushion, spring and guide ring which may be used to help distribute deceleration loading experienced by the syringe subassembly.

6 Claims, 15 Drawing Sheets

U.S. PATENT DOCUMENTS

| | | | |
|---|---|---|---|
| 3,982,651 | A | 9/1976 | Braun et al. |
| 4,031,893 | A | 6/1977 | Kaplan et al. |
| 4,044,933 | A | 8/1977 | Artz |
| 4,226,235 | A | 10/1980 | Sarnoff et al. |
| 4,365,390 | A | 12/1982 | Kageyama et al. |
| 4,367,737 | A | 1/1983 | Kozam et al. |
| 4,394,863 | A | 7/1983 | Bartner |
| 4,578,064 | A | 3/1986 | Sarnoff et al. |
| 4,658,830 | A | 4/1987 | Sarnoff |
| 4,723,937 | A | 2/1988 | Sarnoff et al. |
| 4,795,433 | A | 1/1989 | Sarnoff |
| 5,078,680 | A | 1/1992 | Sarnoff |
| 5,085,641 | A | 2/1992 | Sarnoff et al. |
| 5,092,842 | A | 3/1992 | Bechtold et al. |
| 5,102,393 | A | 4/1992 | Sarnoff et al. |
| 5,137,516 | A | 8/1992 | Rand et al. |
| 5,147,323 | A | 9/1992 | Haber et al. |
| 5,176,643 | A | 1/1993 | Kramer et al. |
| 5,232,459 | A | 8/1993 | Hjertman |
| 5,267,963 | A | 12/1993 | Bachynsky |
| 5,358,489 | A | 10/1994 | Wyrick |
| 5,417,326 | A | 5/1995 | Winer |
| 5,540,664 | A | 7/1996 | Wyrick |
| D375,789 | S | 11/1996 | Bryant et al. |
| 5,578,014 | A | 11/1996 | Erez et al. |
| 5,584,815 | A | 12/1996 | Pawelka et al. |
| 5,665,071 | A * | 9/1997 | Wyrick .................. 604/134 |
| 5,695,472 | A | 12/1997 | Wyrick |
| 5,722,956 | A | 3/1998 | Sims et al. |
| 5,833,669 | A | 11/1998 | Wyrick |
| 6,068,421 | A | 5/2000 | Pierpont |
| 6,210,369 | B1 | 4/2001 | Wilmot et al. |
| 6,312,412 | B1 | 11/2001 | Saied et al. |
| 6,387,078 | B1 * | 5/2002 | Gillespie, III ................ 604/181 |
| 6,405,912 | B2 | 6/2002 | Giannou |
| 6,478,780 | B1 | 11/2002 | Shields |
| 6,508,801 | B1 | 1/2003 | Fineberg |
| 6,562,002 | B1 | 5/2003 | Taylor et al. |
| 6,595,362 | B2 | 7/2003 | Penney et al. |
| 6,613,017 | B1 | 9/2003 | Mickley |
| 6,641,015 | B2 | 11/2003 | Huggins, Jr. |
| 6,678,014 | B1 | 1/2004 | Jin et al. |
| 6,726,649 | B2 | 4/2004 | Swenson et al. |
| 6,796,963 | B2 | 9/2004 | Carpenter et al. |
| 6,986,760 | B2 | 1/2006 | Giambattista et al. |
| 7,297,136 | B2 | 11/2007 | Wyrick |
| 2001/0030196 | A1 | 10/2001 | Stull et al. |
| 2003/0004467 | A1 | 1/2003 | Musick et al. |
| 2003/0014018 | A1 | 1/2003 | Giambattista et al. |
| 2003/0106824 | A1 | 6/2003 | Wilmot et al. |
| 2004/0039336 | A1 | 2/2004 | Amark et al. |
| 2004/0069667 | A1 | 4/2004 | Tomellini et al. |
| 2004/0133159 | A1 | 7/2004 | Haider et al. |
| 2004/0182736 | A1 | 9/2004 | Mesa et al. |
| 2004/0211806 | A1 | 10/2004 | Wilkerson et al. |
| 2005/0148933 | A1 | 7/2005 | Raven et al. |
| 2005/0187519 | A1 | 8/2005 | Harris et al. |
| 2006/0129122 | A1 | 6/2006 | Wyrick |
| 2007/0017532 | A1 | 1/2007 | Wyrick |
| 2007/0017533 | A1 | 1/2007 | Wyrick |
| 2007/0031619 | A1 | 2/2007 | Mirabell |
| 2008/0214996 | A1 | 9/2008 | Kimmell et al. |

FOREIGN PATENT DOCUMENTS

| | | |
|---|---|---|
| EP | 2067496 A1 | 10/2009 |
| TW | 155687 | 4/1991 |
| WO | WO 94/27660 | 12/1994 |
| WO | 9930759 A2 | 6/1999 |
| WO | 03099358 A2 | 12/2003 |
| WO | PCT/US10/000682 IPRP | 9/2011 |

OTHER PUBLICATIONS

Sampson, H.A., "Anaphylaxis and Emergency Treatment," Pediatrics 111:1601-1608 (2003).

Korenblat, P. et al., "A Retrospective Study of Epinephrine Administration for Anaphylaxis: How Many Doses Are Needed?", Allergy Asthma Proc. 1999; 20:383-386.

Merck Manual, 17th Ed., 1053-1054 (1999).

Sampson, H.A. et al., "Fatal and Near-Fatal Anaphylactic Reactions to Food in Children and Adolescents," N. Engl. J. Med. 1992;327:380-394.

EP 05853152.6-1265 Supplementary Search Report dated Feb. 5, 2008.

Taiwan Patent Application 0941319817 Preliminary Examination Report dated Dec. 10, 2007.

WO PCT/US05/43309 IPER, Nov. 15, 2006, Washington Biotech Corporation.

WO PCT/US05/43309 Search Report, Jun. 22, 2006, Washington Biotech Corporation.

WO PCT/US05/43309 Written Opinion, Jul. 5, 2006, Washington Biotech Corporation.

WO PCT/US05/44159 IPRP, Jun. 13, 2007, Washington Biotech Coporation.

WO PCT/US05/44159 Search Report, Feb. 28, 2006, Washnigton Biotech Corporation.

WO PCT US05/44159 Written Opinion, Mar. 3, 2006, Washington Biotech Corporation.

WO PCT/US05/44190 IPRP, Jun. 13, 2007, Washington Biotech Corporation.

WO PCT/US05/44190 Search Report, May 13, 2006, Washington Biotech Corporation.

WO PCT/US05/44190 Written Opinion, May 15, 2006, Washington Biotech Corporation.

WO PCT/US06/07097 IPRP, Jan. 10, 2008, Washington Biotech Corporation.

WO PCT/US06/07097 Search Report, Mar. 1, 2007, Washington Biotech Corporation.

WO PCT/US06/07097 Written Opinion, Mar. 2, 2007, Washington Biotech Corporation.

WO PCT/US10/000682 Search Report, Aug. 2, 2010, Washington Biotech Corporation.

WO PCT/US10/000682 Written Opinion, Aug. 2, 2010, Washington Biotech Corporation.

* cited by examiner

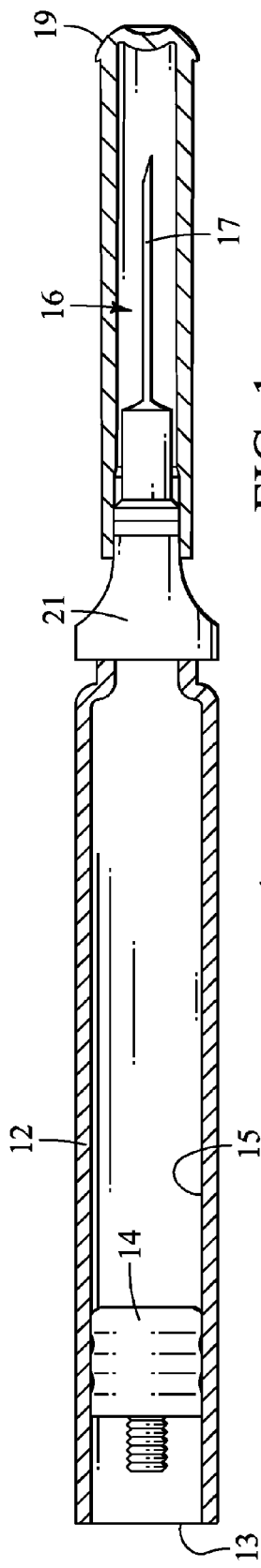
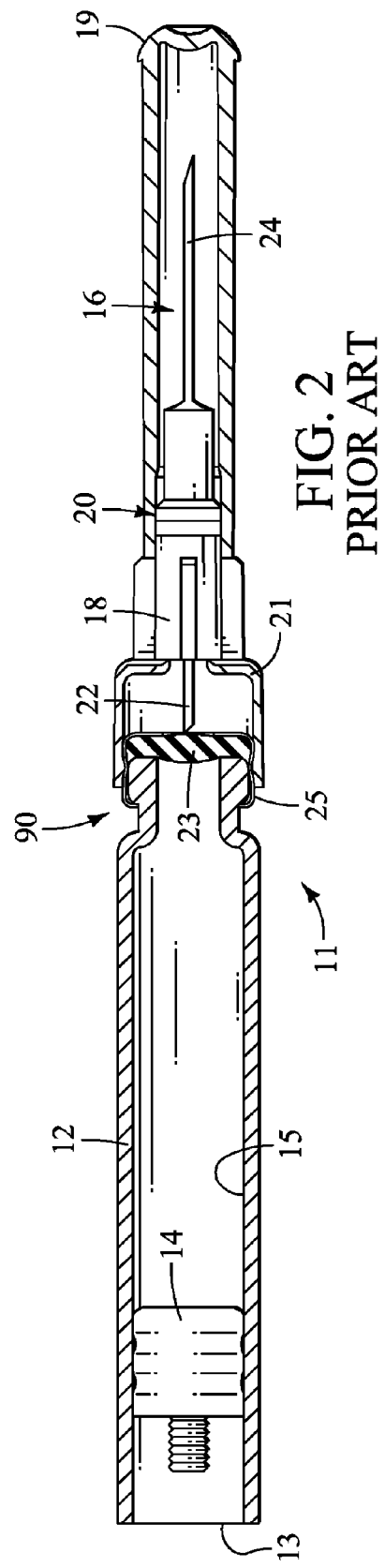

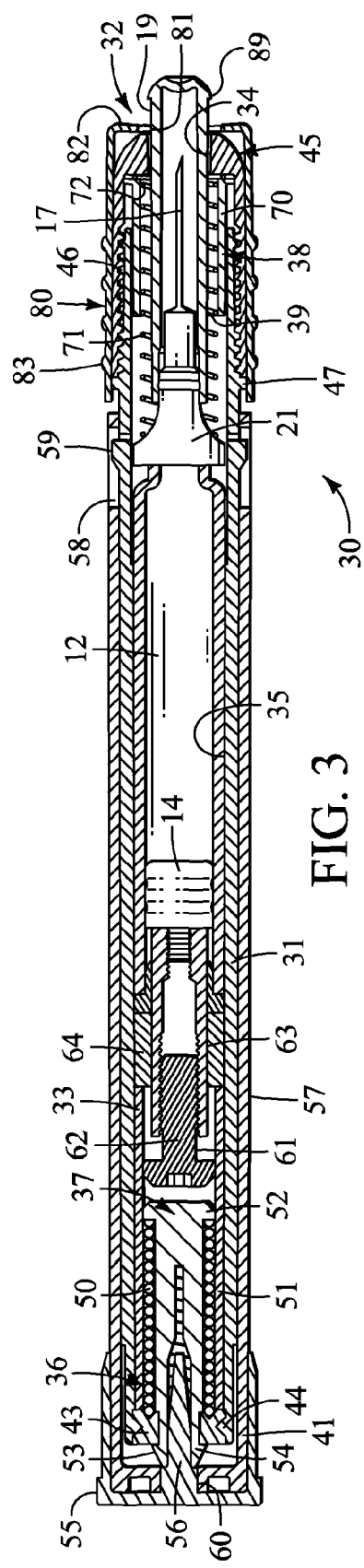
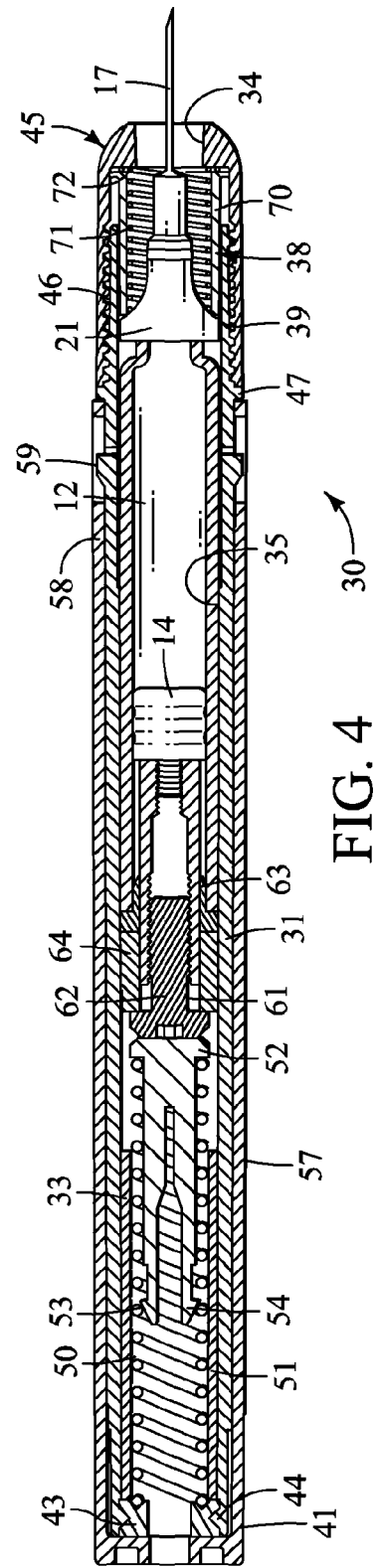

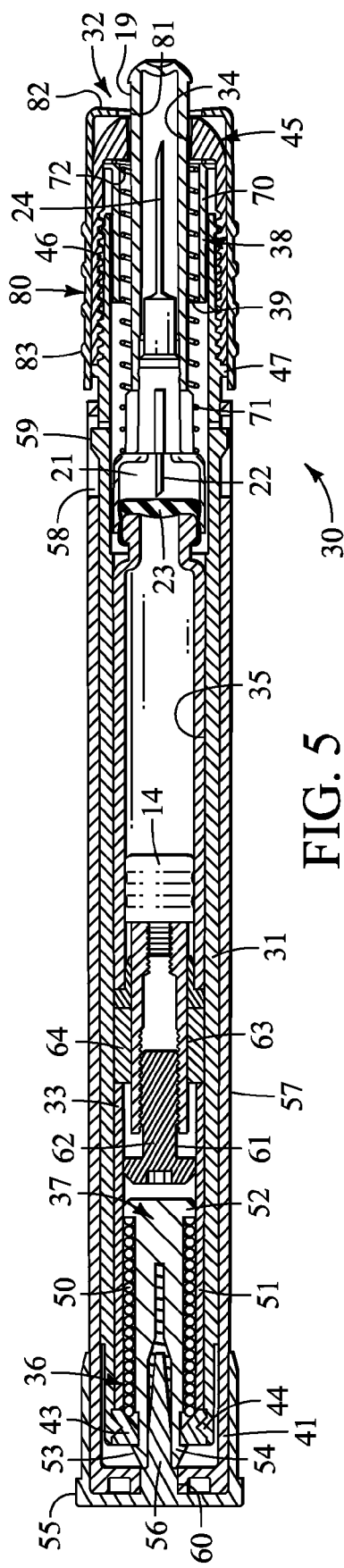
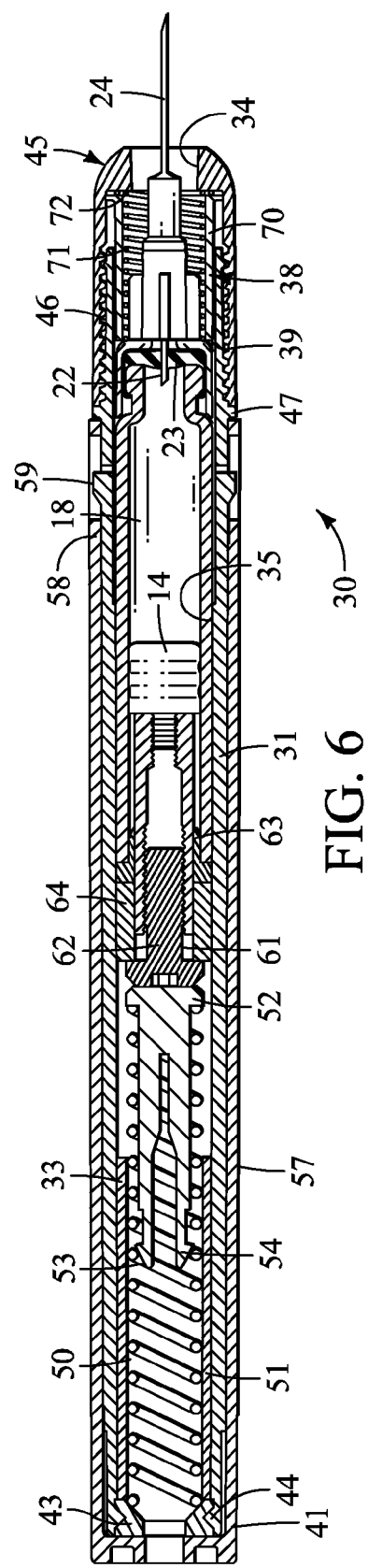
FIG. 5
FIG. 6

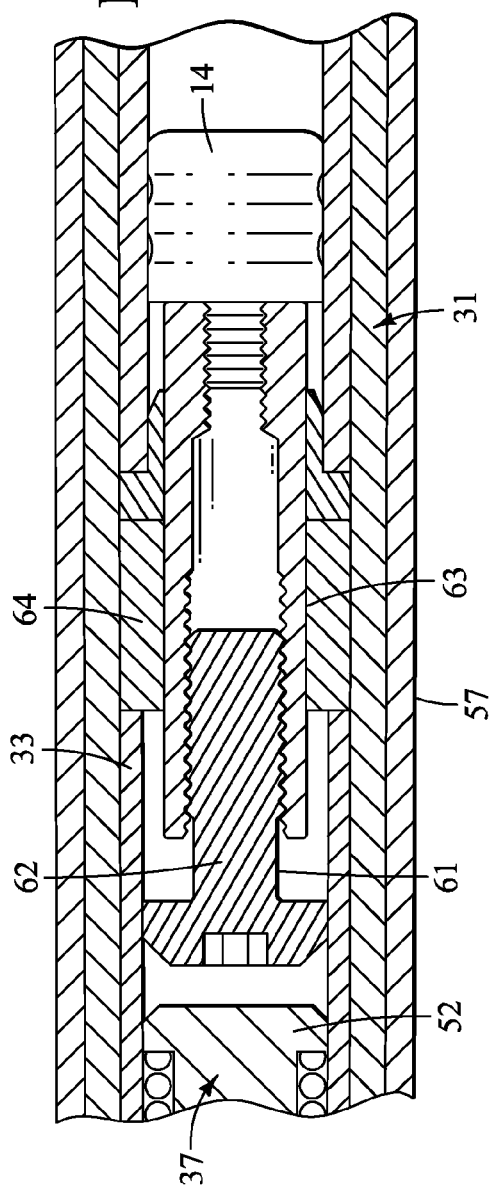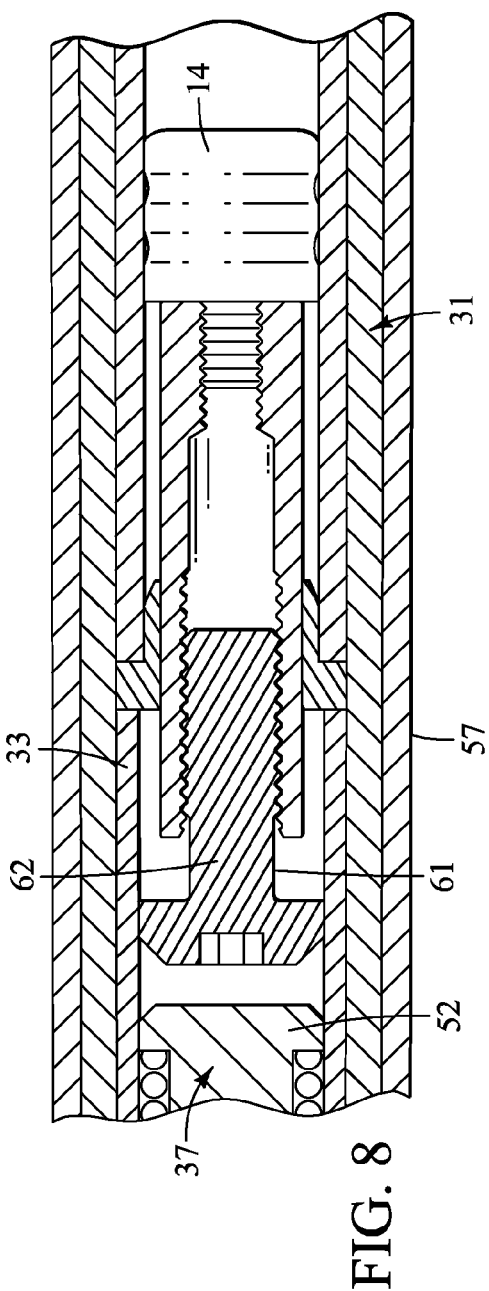

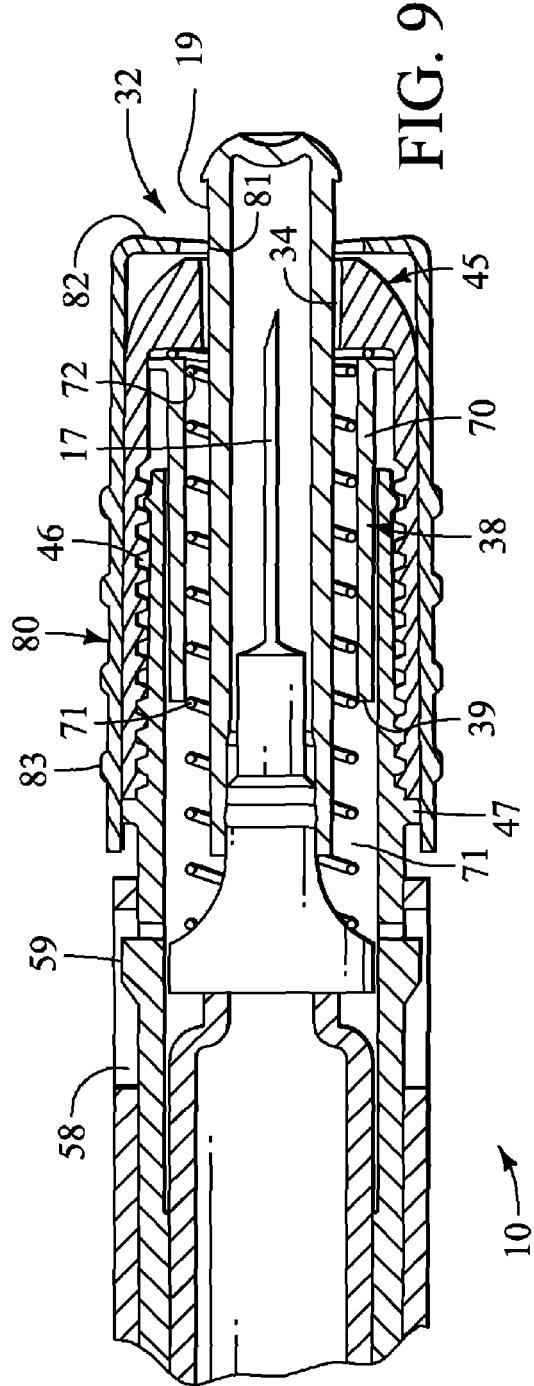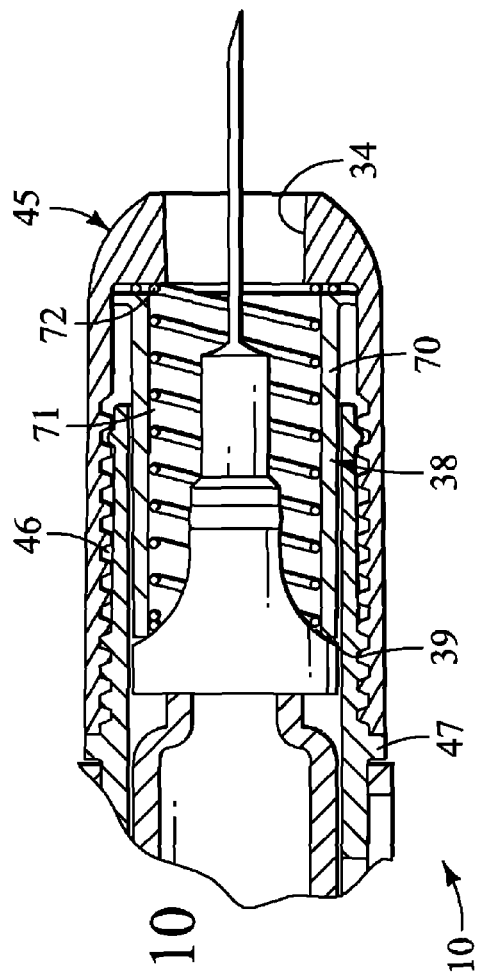

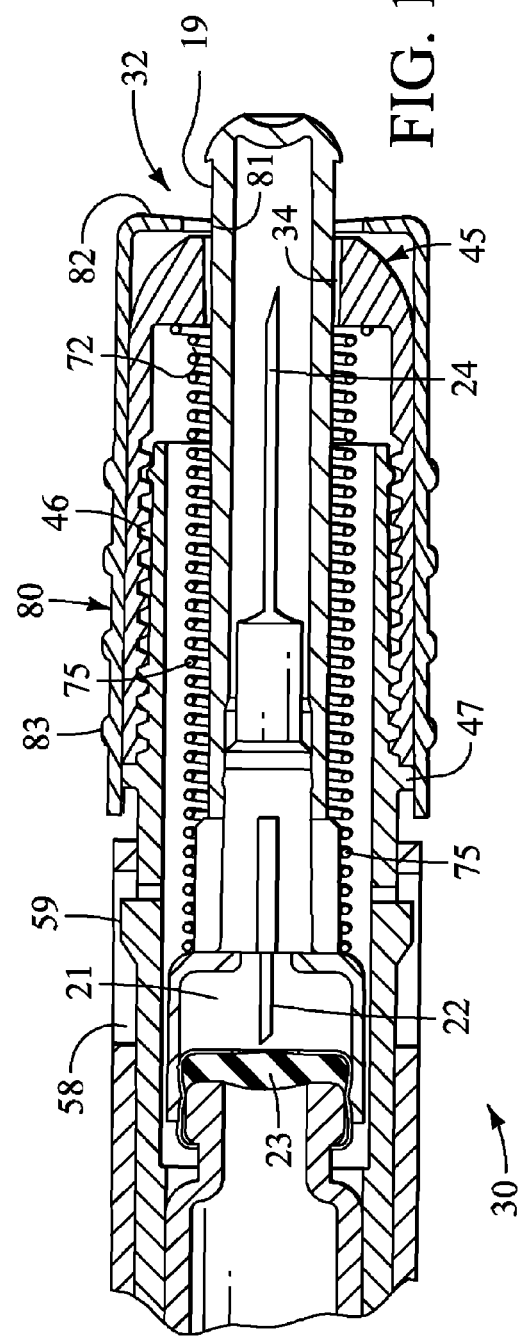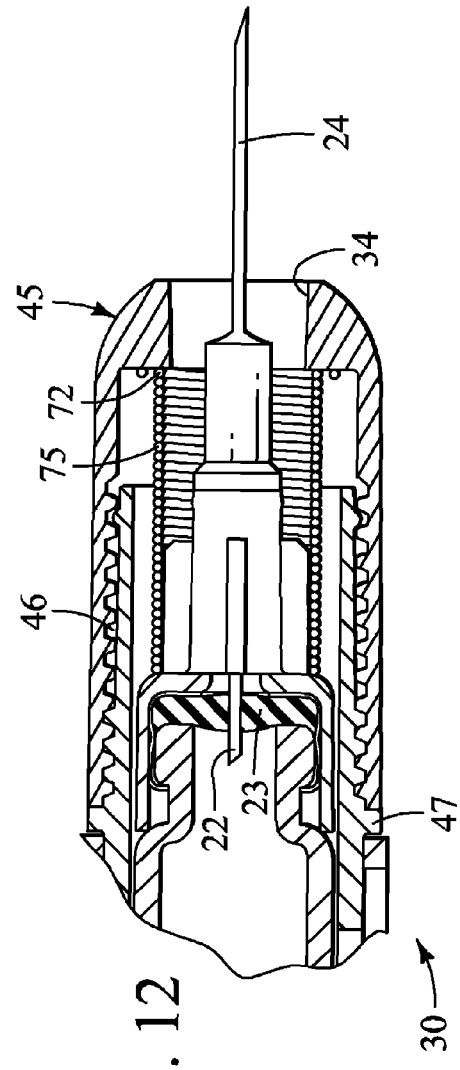

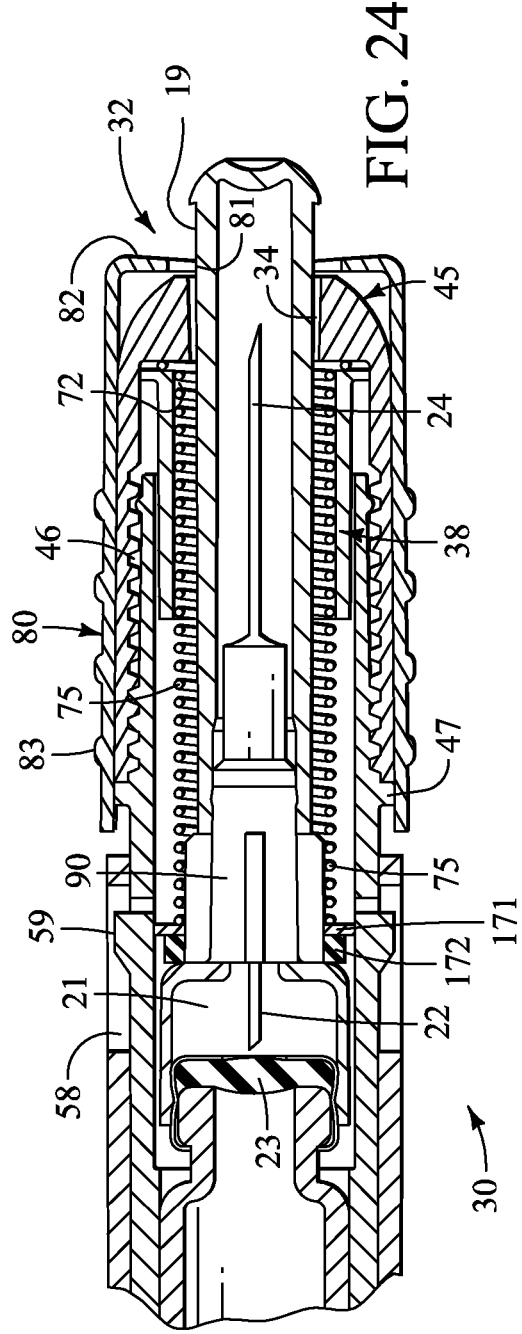
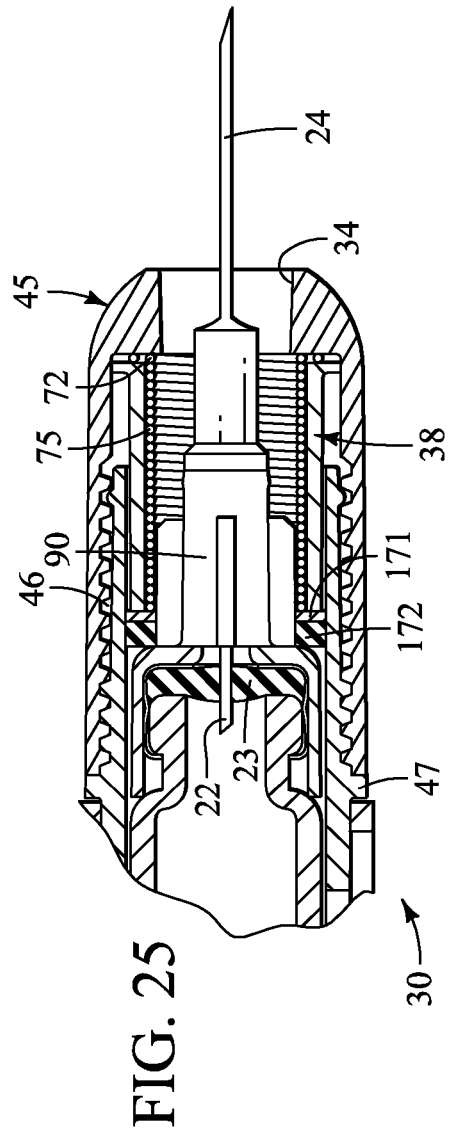
FIG. 24
FIG. 25

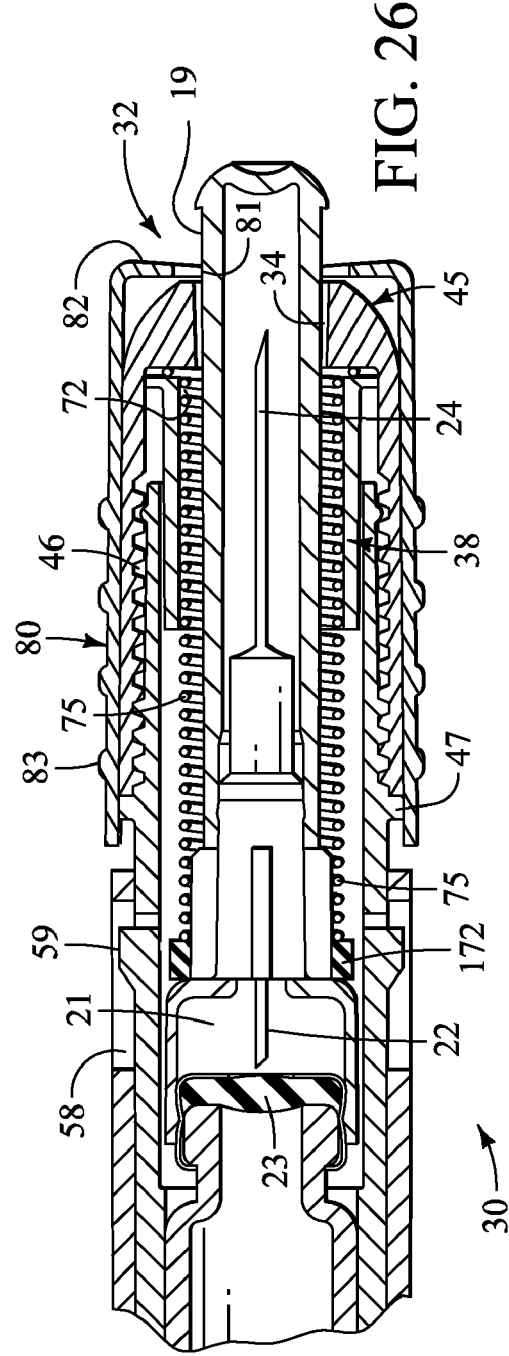
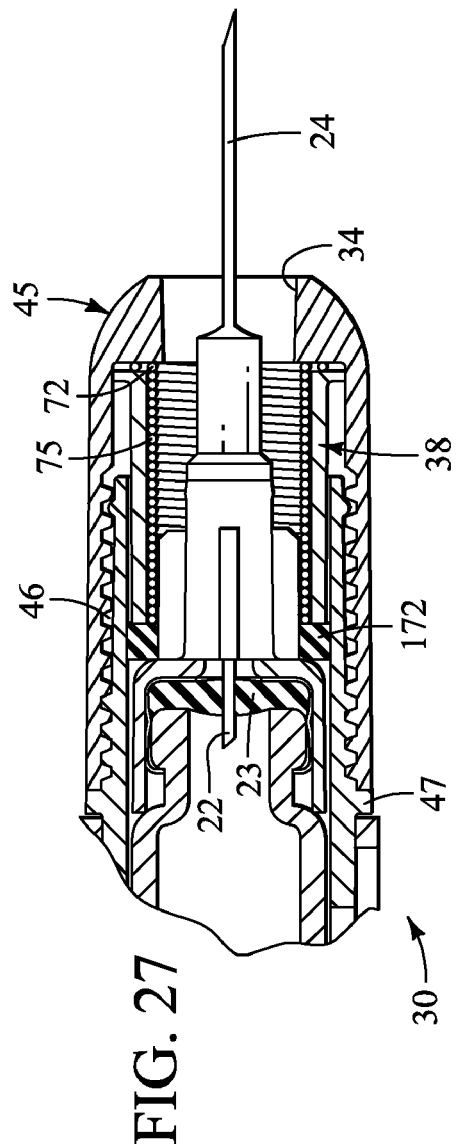
FIG. 26
FIG. 27

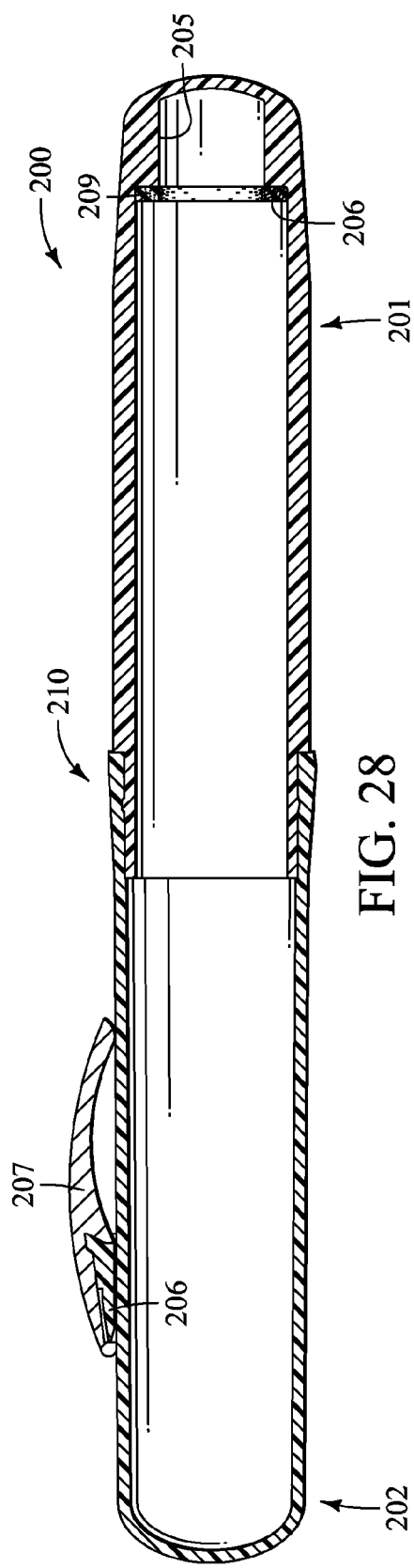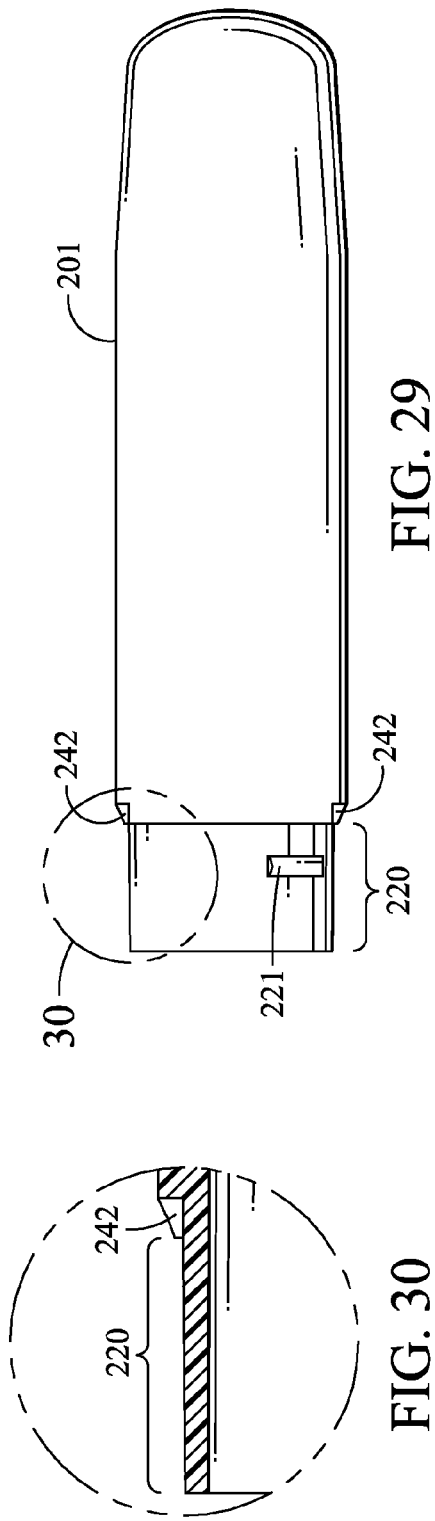
FIG. 28
FIG. 29
FIG. 30

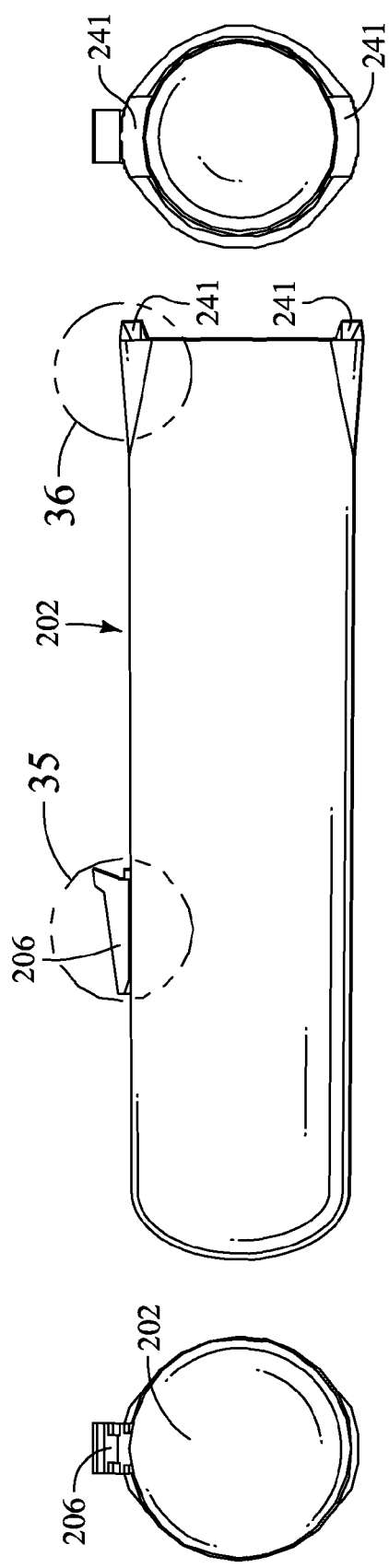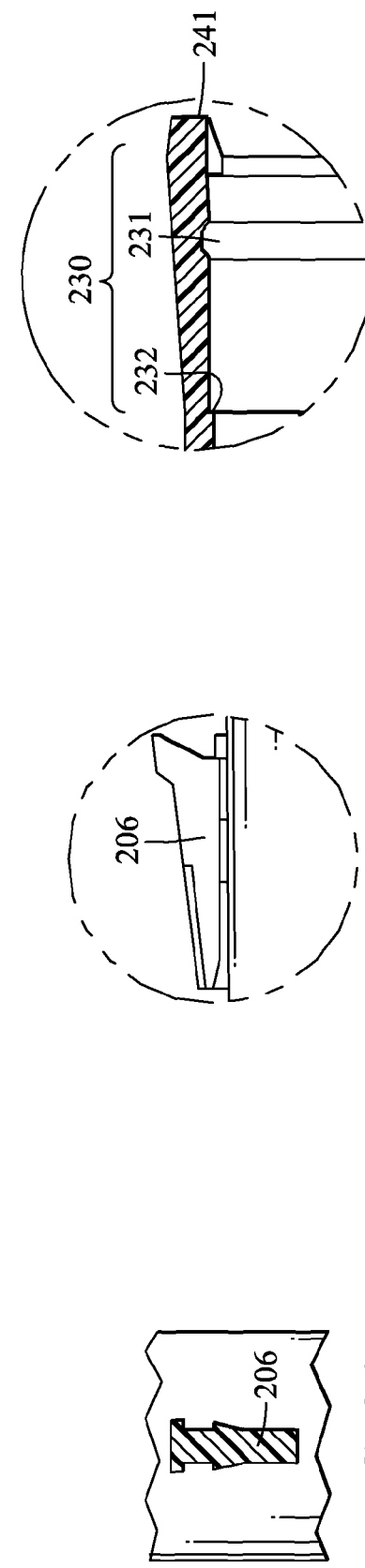

METHODS PERFORMED BY MEDICINE INJECTION APPARATUSES

RELATED APPLICATION DATA

This application is a continuation of U.S. patent application Ser. No. 11/982,397, filed Oct. 31, 2007, now U.S. Pat. No. 7,931,618, issued Apr. 26, 2011, which in turn is a divisional of U.S. patent application Ser. No. 11/006,382, filed Dec. 6, 2004, now U.S. Pat. No. 7,297,136, issued Nov. 20, 2007. This document claims priority to the aforementioned priority applications under 35 U.S.C. §120. The foregoing priority applications are also hereby incorporated by reference herein in their entirety.

TECHNICAL FIELD

This invention relates to injection apparatus and injection of medications into body tissues.

BACKGROUND OF THE INVENTION

Self-administering a hypodermic medicine injection is a difficult task for many individuals to accomplish. Some individuals experience an aversion to driving a needle into the flesh. The result is that many individuals who have health conditions which require periodic injections or who face an emergency need for self injection, or a need to administer an injection on another human or animal will hesitate or in some instances grow faint at the prospect. At least part of the revulsion may stem from watching the needle penetrate the flesh. Another aspect comes from the act of forcing the needle into the flesh. To many, the aversion is so substantial that they simply refuse to either self inject or to administer an injection to another human or animal.

Thus there is a need for a device that will automatically inject medications without requiring the administering individual to watch the needle penetrate, and without requiring that the individual actually supply the force needed to drive the needle into the flesh and dispense medicine into the recipient.

Various automatic injection apparatus have been previously developed. Such apparatus may be used to self administer or to administer, injections to others, in such a manner that the apparatus only requires triggering. Mechanisms provided within the apparatus automatically drive the needle and dispense the medication. Many prior forms of automatic injectors are single use, although some allow for reloading of hypodermic cartridges in which an ampule is provided with a single, fixed needle that openly communicates with the medication in the ampule.

There is also a need for an automatic form of injector that will accommodate double needle injection cartridges in which two oppositely facing needles are slidably mounted by a hub on a medication ampule. A rearward facing one of the needles is situated adjacent a penetrable seal on the ampule so that forced motion of the syringe assembly will result in the rearward needle piercing the ampule seal and allowing the medication to flow to and out the forward needle. Such action, to be most beneficial, should be accomplished by the automatic injector.

Another need is for an automatic injector that can be adjusted for different penetration depths, from superficial to subcutaneous to intramuscular and deeper penetration depths. This varies according to the condition of the patient and/or the medication being administered. This is not just a need related to automatic injectors, but also for individuals who are unaware of penetration depth requirements.

Need also exists for automatic injectors that can be reloaded with conventional ampules to allow for administration of multiple doses. Such injectors allow for removal and replacement of the ampules and re-use of the injector mechanism. Another mode of use is as a single ampule for one injection to give a first dose, and then to reset the injector for a second injection from the same ampule for a second or other multiple doses.

Another pertinent need is the ability to remove the syringe subassembly from the injection device. This may be needed when the injection device malfunctions or when immediate administration of a second or subsequent dose is required.

Some or all of the above needs and others are addressed in part or fully met by various embodiments of the present invention as described below.

BRIEF DESCRIPTION OF THE DRAWINGS

Preferred embodiments of the invention are described below with reference to the following accompanying drawings.

FIG. 1 is a side sectional view of a conventional prior art hypodermic syringe subassembly of the single needle variety.

FIG. 2 is a side sectional view of a conventional prior art double needle syringe subassembly.

FIG. 3 is a side sectional view of a first embodiment device according to the invention in a cocked condition.

FIG. 4 is a side sectional view similar to FIG. 3 showing the needle in an extended condition.

FIG. 5 is a side sectional view similar to FIG. 3 in which a double needle syringe subassembly is in a cocked condition.

FIG. 6 is a side sectional view similar to FIG. 5 showing the double needle syringe assembly in an extended condition.

FIG. 7 is an enlarged sectional detail view of a dosage adjustment and stop arrangement by which multiple dosages may be administered from the same syringe subassembly.

FIG. 8 is a view similar to the detail view of FIG. 7 showing a stop collar removed and the remaining components of FIG. 7 in position for a second dose.

FIG. 9 is an enlarged sectional detail view of a sleeve penetration control embodiment used in conjunction with a single needle subassembly, with the needle in a retracted position.

FIG. 10 is a view similar to FIG. 9 showing the syringe subassembly engaging the sleeve penetration control and the needle extended to a desired penetration depth.

FIG. 11 is an enlarged sectional detail view of a compression spring penetration control used in conjunction with a double needle subassembly, with the needle in a retracted position.

FIG. 12 is a view similar to FIG. 11 only showing the ampule seal pierced, the compression spring penetration control compressed, and the forward needle in an extended position.

FIG. 24 is an enlarged partial side sectional view of a muzzle end of a preferred injector construction having a resilient pad and load distribution and guide ring positioned between the syringe shoulder. The injector is in a cocked condition with the syringe retracted.

FIG. 25 is a view similar to FIG. 24 with the injector shown with the syringe assembly in an extended position.

FIG. 26 is an enlarged partial side sectional view of another preferred form of the invention in a cocked condition with needle retracted.

FIG. 27 is a partial view similar to FIG. 26 with the injector shown with the syringe assembly in an extended position.

FIG. 28 is a sectional view showing a preferred auto-injector storage case according to the inventions.

FIG. 29 is a side view of a bottom part of the case shown in FIG. 28.

FIG. 30 is an enlarged detail sectional view as shown in circle 30 of FIG. 29.

FIG. 31 is a side view of an upper part of the case shown in FIG. 28.

FIG. 32 is a top end view of the upper case part shown in FIG. 31.

FIG. 33 is a bottom end view of the upper case part shown in FIG. 31.

FIG. 34 is a detail view showing a mounting extension forming part of the upper case part of FIG. 31.

FIG. 35 is a side detail view of the mounting extension used to mount a clip to the upper case part of FIG. 31, taken at circle 35 of FIG. 31.

FIG. 36 is an enlarged sectional view taken at circle 36 of FIG. 31.

DETAILED DESCRIPTION OF THE PREFERRED EMBODIMENTS

Introductory Note

Figure 13:
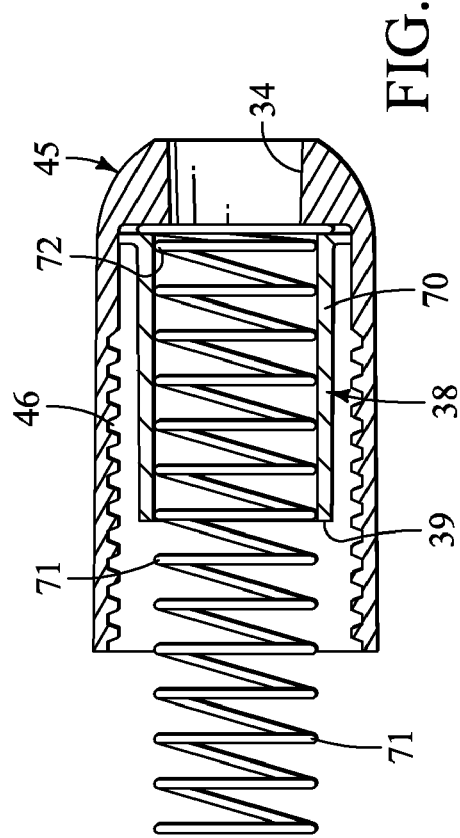
FIG. 13 is a sectional view showing an end cap and penetration control in which any of various length control sleeves can be selected and installed for variably controlling needle penetration to various selected penetration depths.
Figure 14:
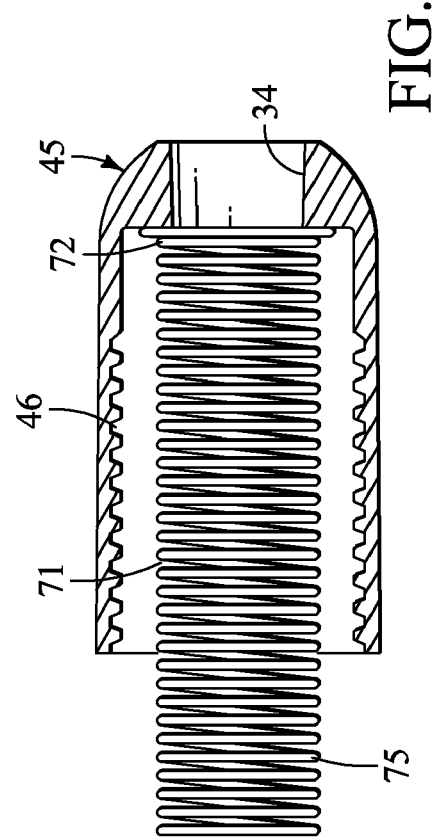
FIG. 14 is a sectional view showing the end cap and one compression spring penetration control installed. Various lengths and other parameters of control springs may be used for controlling needle penetration to various selected depths.

The readers of this document should understand that the embodiments described herein may rely on terminology used in any section of this document and other terms readily apparent from the drawings and language common for such components or operations. This document is premised upon using one or more terms with one embodiment that will in general apply to other embodiments for similar structures, functions, features and aspects of the invention. Wording used in the claims as filed is also descriptive of the invention. Terminology used with one, some or all embodiments may be used for describing and defining the technology and exclusive rights associated herewith.

Syringe Subassemblies

FIGS. 1 and 2 illustrate syringe subassemblies 10 and 11 that are capable of use with the present invention. The illustrated syringe assemblies or subassemblies 10 and 11 are both of known structure and are commercially available. Exemplary commercial subassemblies are manufactured, sold, or distributed under the trademark CARPUJECT™ by Hospira, Inc. Other subassemblies may also be suitable but may require some modification depending on the specifics of construction.

Both subassembly configurations include an ampule 12 that may be a small glass or plastic vial for containing a measured volume of fluid medication, medicament or other injectable substance. The quantity of the substance may be predetermined, based upon the nature of the substance and the anticipated usage. The ampule 12 may be pre-loaded with the substance and provided by the substance producer or distributor.

In both versions, the ampule or vial 12 includes a rearward end 13 that is potentially open to slidably receive a plunger 14. The plunger and plunger piston can be moved axially within the ampule bore 15 by application of axial force against the plunger shaft or rod. The plunger 14 will thus force the substance out through a hollow needle assembly 16 at a forward end of the ampule when the plunger assembly is depressed toward the forward or needle end.

Subassemblies 10 and 11 differ in the construction of their needle assemblies 16. Subassembly 10 (FIG. 1) is of the fixed needle variety in which a fixed hollow needle 17 is mounted by a fixed hub 21 to the associated ampule 12. The needle 17 openly communicates with the substance within the ampule and will eject the substance in response to forced contractionary motion of the plunger 14. A sheath 19 may be included to releasably cover the fixed needle 17 for sanitary and safety reasons, and must be removed or be pierced by the needle before administration of the injection.

Needle assembly 16 for syringe subassembly 11 (FIG. 2) differs from the fixed needle assembly structure described above. Syringe subassembly 11 makes use of a double needle assembly 20 in which a double needle hub 90 or 21 mounts a seal penetration needle 22 that projects rearwardly toward a penetrable seal 23 on the associated ampule. Flesh penetration needle 24 projects forwardly. In practice, both needles 22 and 24 can be made integral. In such an integral construction both needles may be formed of the same needle tube, sharpened at both ends and immovably fixed to needle assembly hub 90.

Hub 90 mounts both needles 22 and 24 and has a cup-shaped receptacle for receiving the sealed end of the ampule. It also preferably has features or provisions to mount the needles in axial sliding relation to a seal retainer 25 of the associated ampule 12. Forced sliding movement of the ampule relative to hub 90 will thus cause the seal penetrating needle 22 to engage and then pierce the penetrable seal 23. Once seal 23 is pierced, the substance within the ampule may be forced through the needle or needles 23 and 24 as the injection is administered.

The double needle subassembly 11 may also make use of a protective needle sheath 19. The sheath can vary or be substantially similar, or even identical to that used for the single needle subassembly 10. For either form of subassembly, the sheath may be provided as a rigid cover, or as a flexible member that may be penetrated by the adjacent needle upon application of sufficient axial force. This is disclosed in my earlier issued U.S. Pat. Nos. 5,540,664 and 5,695,472; such disclosures being hereby incorporated by reference into this application. Also incorporated by reference are my earlier U.S. Pat. Nos. 5,358,489 and 5,665,071.

Injection Device

General Configuration

A reloadable hypodermic injection device according to the invention is shown in the drawings and is identified therein by reference numeral 30. Injection device 30 (FIGS. 3-6) includes a barrel 31 having a muzzle end 32, with a needle receiving aperture or passageway 34. A syringe subassembly receiving cavity 35 is situated along and within the barrel 31, and is preferably adjacent to and accessible from the muzzle end 32. The cavity 35 is adapted to releasably and slidably receive a syringe subassembly 10 or 11 for movement toward and away from the muzzle end 32. The needle assembly 16 is aligned to project through the needle receiving aperture 34 or through a protective septum (not shown) positioned across and similar to aperture 34.

A syringe driver 36 has an actuator or driver contact 37 that is movable toward the muzzle end 32 extending into the syringe subassembly receiving cavity 35. A penetration controller 38 or other penetration control is also advantageously provided. The penetration controller may include a penetration control abutment surface 39 which engages the ampule assembly, such as at a shoulder or other appropriate feature thereof. The penetration controller has a suitable length and configuration from the muzzle end 32 to provide a desired needle penetration depth or forward needle stop position.

The Barrel

As set forth by example in the drawings, barrel 31 is elongated and tubular, defining the subassembly receiving cavity 35 between a rearward end 41 and the muzzle end 32. The barrel may be formed of plastic or any other suitable medically acceptable material of suitable strength.

A driver guide or driver spring guide 33 can be integral with or fitted as a sleeve within the barrel 31 to maintain the driver spring or other driver force generator in a desired position, such as coaxially positioned therein. As shown, guide 33 functions to guide extension and retraction of the syringe driver spring 36. Guide 33 as shown also advantageously functions as a positioner to accurately locate the syringe assembly 10, 11 coaxially within the barrel 31.

In the illustrated forms, the rearward barrel end 41 is adapted to mount an annular end piece or firing bushing 43 which is used in conjunction with the driver 36, details of which will be described further below. To facilitate assembly, the barrel rearward end 41 is preferably molded about an inward annular ridge 44. It may alternatively be possible to produce each part separately and have the annular ridge snap fit with the firing bushing 43.

The muzzle end 32 in preferred forms mounts a separable nose cap 45 that defines the needle aperture 34 or other passageway through which the forward needle extends when fired. The aperture or needle puncture location of the nose cap 45 can be releasably attached to the barrel by means of interfitting threads 46, rings or other projections. Cap 45 may thus be separated from the barrel to permit access to the barrel cavity 35, thereby permitting insertion and removal of the needle subassemblies 10 or 11.

Syringe Driver

Driver 36 is used to operate against or be connected through a plunger rod 61 to the plunger or plunger piston 14 of the needle subassembly 10 or 11. The plunger rod may be separable or integral with the plunger piston. The driver is functional to force the subassembly in a forward direction to effect needle penetration and to operate against the plunger to inject the ampule contents. Such forces are automatically applied by spring or other suitable driver force initiated through a triggering operation initiated by the user.

Driver 36 as exemplified herein includes the driver bar or shaft 37 (FIGS. 3, 4) which is shown within the barrel 31 in a rearwardly cocked position by a driver release mechanism 53 that may be similar or identical to that shown in U.S. Pat. Nos. 5,540,664 and 5,358,489 which are incorporated by reference herein.

Notwithstanding the above incorporated materials, a preferred driver is further exemplified herein as including a drive spring 50 that is compressed when ready or cocked. The drive spring 50 is preferably guided and contained within the barrel by a spring guide which is advantageously in the form of a guide sleeve 51. As shown, the guide sleeve is tubular with the guide spring extensible within tubular guide sleeve 51 with portions of the spring slidable therewithin. Other configurations may also be suitable.

The drive spring is selected to provide sufficient stored energy when compressed to force the needle subassembly forwardly against downstream resistance and perform needle penetration and injection functions. It serves to displace the plunger 14 and thus expel the medicament contained in the ampule 12 through the injection needle 17.

The drive spring 50 acts against and is restrained by the firing bushing 43 at one end. The opposing end bears upon the driver bar 37 which engages the plunger rod 61. The exemplified driver bar or shaft 37 provides a spring engagement shoulder 52 (see FIG. 3) against which the forward end of driver spring 51 engages. As shown, driver release 53 includes a barb or barbs 54 that fit through the firing bushing 43 central aperture. The barbs are preferably formed on flexible ends of the legs of the driver bar or shaft 37.

A safety, advantageously in the form of a safety cap 55, has a forwardly projecting pin 56 that is received between the legs of the driver shaft or stem to hold the barbs 54 in engagement with the firing bushing 43 and thereby prevent forward movement of the driver bar 37 until the safety is removed. The safety or safety cap 55 can be pulled rearwardly to slide the tapered safety pin 56 from between the legs of the driver bar. This frees the barbs to be forced inwardly and radially together. As shown, the barbed legs of driver bar 37 are moved inward by the rearward or end of firing sleeve 57 as will be further detailed below. The firing sleeve 57 acts as a trigger.

Figure 20:
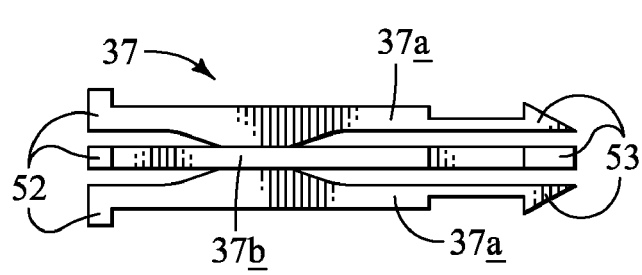
FIG. 20 is a side view of a driver shaft construction having four legs.
Figure 21:
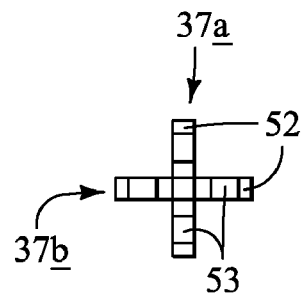
FIG. 21 is an end view of the driver shaft of FIG. 20.

FIGS. 20 and 21 show the preferred driver shaft or stem has four legs, although other numbers are believed possible. The driver shaft or stem is preferably made using two parts 37a and 37b which fit together. These parts can alternatively be made of metal and be molded or otherwise formed as an integral piece.

Radial inward movement of the barbed legs causes the barbs 54 to move into a release position as effected by an exterior firing sleeve 57. In the design illustrated, the firing sleeve extends over and along the outside of the barrel. The exposed length of the firing sleeve allows the user to grasp the injector by the firing sleeve when the injection is to be administered.

A forward end of the firing or trigger sleeve can include slots 58 (see FIGS. 4-6, 9 and 10) that slide along retainers 59 formed on the forward end of the barrel. The retainers are advantageously in a peninsular configuration that provides flexibility to retainers 59 for assembly or possible disassembly. The interaction between retainers 59 and slots 58 prevent the firing sleeve from being unintentionally removed from the barrel. Such interaction also limits the extent of axial relative movement while also allowing the parts to be assembled or disassembled by depressing retainers 59.

The firing sleeve 57 includes a trigger head having an opening 60 (FIGS. 3-6) which is preferably centrally located. The trigger head of sleeve 57 is advantageously beveled along the contact area with barbs 54. Opening 60 receives and inwardly cams the barbs 54 on the legs of the driver bar 37. This forces the barbed ends together once the safety cap is removed and the firing sleeve is moved forwardly with respect to the barrel. Such action triggers the driver release 53 to free drive spring 50. Drive spring 50 thus extends longitudinally, driving the driver bar 37 into the plunger shaft and forcing the syringe subassembly forwardly to administer the injection.

FIGS. 3-6, 7 and 8 show that the driver bar 37 is configured to push against an adjustable plunger rod 61 which is attached to the plunger 14. The plunger shaft assembly may be part of the syringe subassembly 10 or 11. Alternatively, the plunger shaft or rod 61 may be produced as an integral part of the driver or as a separate assembly or part. The plunger shaft may also be made in a non-adjustable configuration, such as solid or as a non-adjustable assembly.

In the illustrated embodiments, the plunger rod 61 is advantageously made up of two axially adjustable components including an actuator or driver engaging section 62 and a plunger engaging section 63. As shown, sections 62 and 63 are threadably engaged to allow for adjustment of the overall length of rod 61. This is used to help adjust the dosage or volume of material dispensed during a single operation of the injection apparatus.

The illustrated plunger rod 61 is advantageous in that the two axially adjustable sections 62, 63 allow for longitudinal rod length adjustment, and for threaded or other connection to the plunger 14. Section 62, as shown, has a head portion and threads which are received into section 63. Plunger rod section 63 is coupled, such as by threads, or is otherwise attached to plunger 14. Relative rotation of the two sections 62 and 63 can effectively change the plunger rod length, thereby allowing for accurate dosage adjustment, even though the syringes vary in length until adjusted to have the same or other desired length.

It is also possible that a different, conventional form of plunger rods (not shown) might be provided as a part of the syringe subassemblies 10 or 11. In such an alternative construction the adjustable rod 61 may not be needed or used. In such a construction, dosage adjustment may be sufficiently accurate by using a properly selected stop collar 64 which will be discussed further below. In either construction, plunger rod 61 or an alternative integral plunger rod (not shown) can be provided with or as a part of the plunger assembly. With an adjustable plunger rod, such as provided by parts 62 and 63, dosage control is more accurate since each ampule may vary in length and the adjustment capability can accommodate for such variations. This may be needed when medicaments are to be dispensed in very accurate dosage amounts. Other medicaments may not be sufficiently sensitive to dosage amounts and the adjustable plunger costs and adjustment in production may not be needed or justified.

Dosage Adjustment

The present device is capable of use for single or for multiple injections. To enable such use, one or more stops in the form of dose stop collars 64 (FIG. 7) can be releasably mounted to the driver 36 or, in the illustrated example, to the plunger rod 61. In the illustrated embodiments, one such collar 64 is shown attached to the rod 61 rearward of the ampule 12, and forward of the headed section 62 of the plunger rod. The collar 64 and possible multiple such collars are advantageously positioned in the forward path of the headed end of the plunger rod 61. Collar or collars 64 stop forward motion of the plunger rod at such point where a selected first dosage has been expelled from the syringe subassembly 10 or 11.

If a second dose remains within the ampule following the first injection, the syringe subassembly 10 or 11 can be removed from the barrel to gain access to collar 64, which then can be removed from the plunger rod 61 to permit further motion of the plunger to deliver the additional dose.

Following removal of the syringe and collar, the syringe driver 36 can be recocked, but the process of recocking requires holding the barrel 31 in reaction to the force needed to recompress the drive spring 50. This may be difficult in the constructions shown and described herein due to the firing sleeve or trigger handle 57 extending over the majority of the length of the barrel 31. In other embodiments or with care the syringe can be recocked by holding the barrel and inserting a screw driver or similar tool and depressing the driver bar 37 and associated driver spring 50. If recocked, the syringe subassembly can be re-inserted into the barrel for automatic injection of a second or another dose which becomes available as the plunger is permitted further forward travel in response to subsequent triggering.

The length dimension of the collar 64 or multiple collars can be selected according to the desired dosages to be administered. Although not illustrated, multiple collars may be stacked along the plunger rod, with each collar representing a dose of medicament or other substance from the ampule. Separate injections may be performed following removal of successive stop collars. Alternatively, in instances where single dosages are desired, a single or even no stop collar may be selected according to the desired single dosage.

Figure 16:
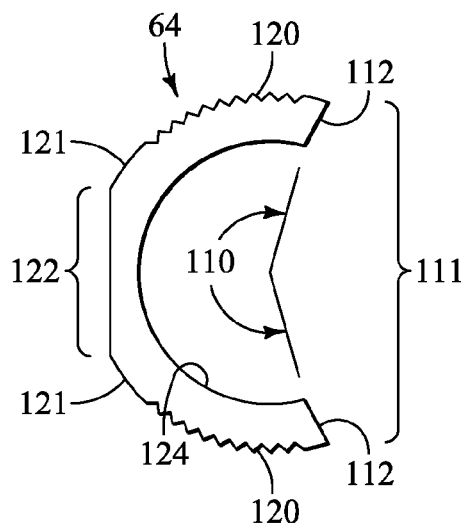
FIG. 16 is a top view of a preferred stop collar.
Figure 17:
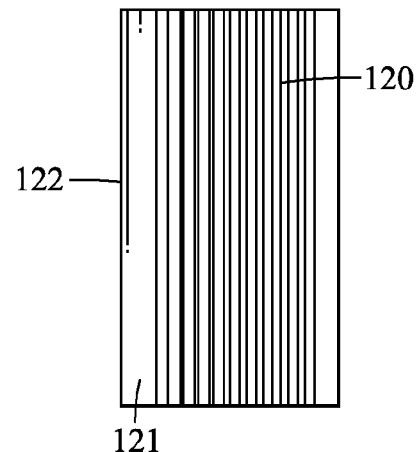
FIG. 17 is a side elevational view of the stop collar of FIG. 16.

Stop collar 64 may be made having different sizes of arcs. In some cases the collars extend fully about the plunger shaft. A currently preferred stop collar has an arcuate size of about 180-200 arcual degrees. FIGS. 16 and 17 show a currently preferred design having an open side and an arcuate size 110 of about 185-190 arcual degrees. The relatively open side 111 is advantageously provided with end faces 112 which are beveled to converge inwardly. These features provide easier installation of the stop during production and easier removal by a user after the first or other prior dose has been administered.

Another feature shown in FIGS. 16 and 17 that facilitates removal of stop collar 64 is the provision of ribs, flutes, striations or other friction features 120. These friction features improve manual grasping of the collar to remove it from the outside of plunger shaft 61. This construction allows a user to remove the collar using the thumb and forefinger from a single hand. It improves the removal such that two hands are not necessary as was the case in earlier designs. This improvement greatly reduces the chance that the action of removing the stop collar does not lead to accidental depression or upward movement of the plunger which may compromise the accuracy of the second dose amount.

The outside of the stop collar 64 may also advantageously be provided with circumferential segments 121 between the friction features 120 and a flat segment 122. Flat segment 122 facilitates installation of the stop collar upon the plunger rod 61.

The inside surface 124 is preferably semi-cylindrical and sized to fit the plunger rod 61. The particular size may vary depending on the size of ampule and size and type of plunger rod used.

Nose Cap or Muzzle End Piece

FIG. 6 shows that nose cap 45 is advantageously removable from the barrel to allow insertion and removal of a syringe subassembly. Cap 45 may be generally in a cup shaped form to be received upon the forward end of barrel 31. In the illustrated embodiments, the nose cap fits over the outward surface of the barrel. The nose cap is secured thereon using threads or other suitable connection joint. Depending on the specific construction used, the nose cap may alternatively fit within the barrel.

It is preferred for accuracy in needle penetration depth control that the nose cap 45 be secured axially against a positive stop such as a shoulder 47 formed along the barrel 31. Shoulder 47 can be provided along the barrel to accurately locate an installed nose cap 45 in a repeatable manner. This is preferred to provide axial accuracy to the relative location of the nose cap 45 upon the barrel. This is desirable since the nose cap may be removed and re-mounted repeatedly to enable removal and replacement of ampule and needle subassemblies.

It is advantageous for accurate positioning of the nose cap 45 to use the threads 46. Threads 46 are provided along the nose cap 45 and barrel 31 to facilitate secure engagement between the abutment shoulder 47 and nose cap 45. However, fastening arrangements between the nose cap 45 and barrel 31 may be used other than the illustrated threads 46. For example, a bayonet, barb, snap fit or other releasable connection arrangement could also be used to releasably interlock the nose cap with the adjacent forward part of barrel 31 to provide repeated accurate positioning.

The forward end of nose cap 45 defines the illustrated needle aperture or passageway 34. Aperture or passageway 34 is advantageously sized to receive needle sheath 19 therein. As illustrated in FIGS. 9 and 10, the needle safety sheath can project through the aperture 34. Sheath 19 may be provided with a blunt forward end which may extend forward of the muzzle end 34. The projection of the sheath facilitates removal of the sheath immediately prior to use.

The outside of nose cap 45 may advantageously be provided with ribs, flutes, striations or other friction surface to facilitate installation and removal of the nose cap from the barrel. The construction shown uses a threaded connection between the nose cap and barrel. Thus an exterior friction surface allowing torque to be applied is preferred in such constructions. A preferred friction surface has minute linear longitudinal striations (not shown).

Sheath Remover

Figure 18:
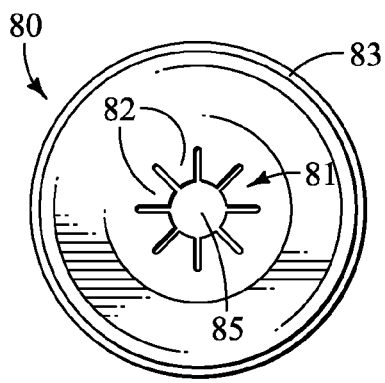
FIG. 18 is an end view of a preferred sheath remover.
Figure 19:
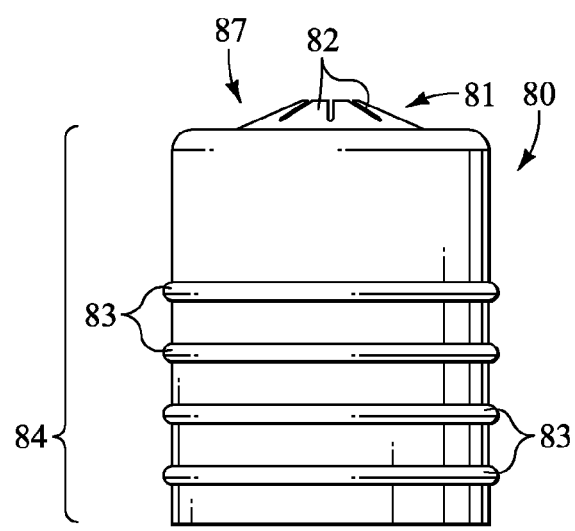
FIG. 19 is a side view of the sheath remover of FIG. 18.

Removal of the sheath 19 from the syringe sub-assembly 10 or 11 can be accomplished or facilitated by provision of a sheath remover 80 that is releasably mounted at the muzzle end 32. FIG. 18 shows an exemplary sheath remover 80 from the forward end. FIG. 19 shows a side view of the sheath remover. The construction illustrated includes a sheath gripper 81. The gripper has a central aperture 85 that is disposed in substantial coaxial relation to the needle receiving aperture 34 of the nose cap. The central aperture 85 receives the sheath 19 therethrough.

Gripper 81 also preferably includes radially inward projecting fingers 82 that flexibly grip the sheath 19 behind a lip 89 (see FIG. 3) near the tip of the sheath remover. The inwardly projecting fingers 82 provide sufficient flexibility to allow the sheath remover to be pushed onto and installed over the enlarged end of the sheath near lip 89.

A collar portion 84 extends rearwardly of the end surface 87 and is received over the nose cap 45. The collar portion 84 may be provided with circumferential ribs 83 to improve manual grasping of the sheath remover so as to facilitate pulling the sheath and sheath remover from the injector.

Fingers 82 will flex rearwardly during removal of the sheath and catch on lip 89 and securely grip the sheath 19 when the remover is pulled forwardly. In doing so, the fingers will catch behind the lip and further bind and pull the sheath 19 from the needle assembly hub 90 (FIG. 3) to expose the outwardly directed needle 17. The sheath and sheath remover can later be re-installed, in an instance where it becomes desirable to re-cover the needle for safety purposes.

Penetration Control

Syringe driver 36, when triggered, forces the syringe subassembly 10 or 11 forwardly within barrel cavity 35. This drives the needle 17 forwardly through the aperture 34 to penetrate the flesh of the patient. Depth of penetration according to the present invention is advantageously determined using a penetration controller 38 (FIGS. 9-15) and other alternative forms described herein. The penetration control or controller stops penetration at a desired repeatable penetration depth of needle 17. This is different than dose control, since the penetration depth is gauged from the nose cap which actually contacts the flesh during automatic injection.

Penetration controller 38 in preferred forms is located along the barrel 31, with an abutment surface 39 spaced from the muzzle end 32 at a selected and desired needle penetration depth stop position. The penetration control is engaged by the syringe assembly to stop forward motion of the flesh penetration needle 17 at the selected penetration depth. This is done to remove the necessity for the user to determine penetration depth. By providing a penetration control, the device can be selected or adjusted so the needle will penetrate only to a desired depth as an automatic function of the device. Adjustment is preferably provided using a penetration sleeve, spring or other penetration control element.

First Exemplary Penetration Controller

Figure 22:
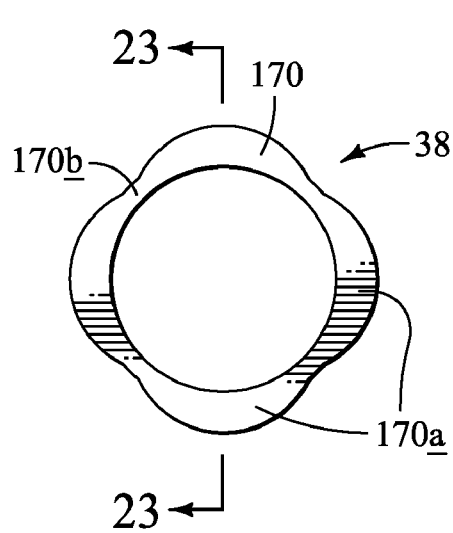
FIG. 22 is an end view of a preferred penetration controller sleeve.
Figure 23:
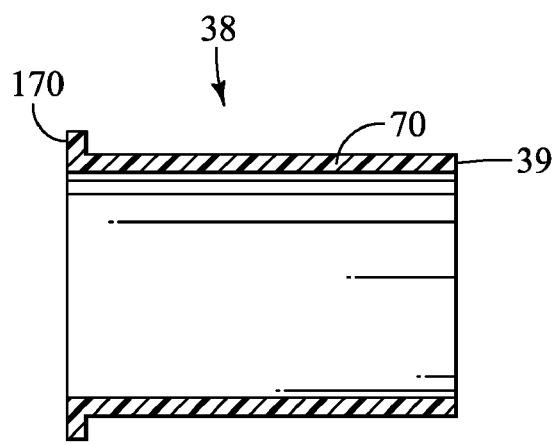
FIG. 23 is a side sectional view of the penetration controller sleeve of FIG. 22 taken along section line 23-23 of FIG. 22.

In one preferred form, the penetration control is provided by penetration controller 38. Penetration controller 38 may be constructed more specifically in the form having a tubular sleeve 70 portion held within the nose cap 45. FIGS. 22 and 23 show penetration controller 38 in detail. The penetration controller includes a control sleeve 70 which has a flange 170 attached thereto. It is advantageous that the sleeve 70 and flange 170 be shaped for frictional engagement within the nose cap 45. This is desirable so that removal of the nose cap will also result in removal of the penetration control 38. This is facilitated by flange lobes 170a which tend to cant within the nose cap cavity (FIG. 22). This mounting arrangement also helps to provide repeatable and accurate axial positioning of the abutment surface 39 within the barrel 31 and relative to the outer front face of the nose cap or other flesh contacting face of the injector. The flange sleeve 70 and thickness of flange 170 define the length of the controller. The end of the sleeve opposite the flange provides a syringe abutment surface 39 at a selected distance from the muzzle end. In this example, the surface 39 is at the rearward end of the sleeve and faces the needle subassembly within the cavity 35.

The overall length of controller 38 is typically defined by the length of sleeve 70. The length may be selected from a group having varying axial dimensions to effect different needle penetration depths. Thus one sleeve may be useful for subcutaneous injections, while another may be selected when deeper intramuscular penetration is required. A selection of sleeves of differing axial lengths may be used dependent upon the medicine being provided in the injector or for specific depths of desired needle penetration.

The sleeve 70 is also useful to receive a forward or return spring 71, preferably of the coiled compression variety, which can be disposed within the barrel, between the nose cap 45 and needle hub. The front or return spring 71 is provided to yieldably resist forward motion of the needle subassembly to hold the subassembly in the retracted position until the syringe driver 36 is triggered. Spring 71 also helps to reduce the impact of the syringe assembly with the penetration control, thus reducing or eliminating breakage of the hub or penetration controller.

The penetration control unit 38 can be used to secure the return spring 71 in position within the barrel, using flange 170. This also helps retain the spring for removal along with the nose cap 45 (FIG. 13). To this end, the spring diameter may be enlarged at its forward end 72 in order to provide a friction fit between the spring 71, sleeve 70 and the nose cap 45, while allowing the remainder of the spring free movement within the confines of the sleeve portion 70.

One of the important functions of the return springs is to keep the needle in a hidden, retracted position after the sheath is pulled off. This prevents the user from seeing the needle and prevents the user from being scared due to needle fright. The return spring acts quickly on removal of the sheath to return the syringe up inside the barrel such that the user has no visual reminder that there is a needle positioned in a hidden position therein.

By providing the return spring 71 and sleeve 70 arrangement described above, the fully compressed axial spring length will be less than the sleeve length. Thus the penetration depth is determined by the selected length of sleeve 70 and flange 170. With proper design, the yieldable resistance offered by spring 70 will remain within suitable limits regardless of the sleeve length selected to adjust penetration depth.

The above arrangement (in which the return spring 71, selected sleeve 70 and flange 170, and nose cap 45 are interconnected) is advantageous to simplify attachment to and removal from the barrel 31. A user wishing to gain access to the needle sub-assembly for replacement or for second injection purposes, need only unthread the nose cap 45 from the barrel end. The return spring 71 and sleeve 70 will move along with the nose cap to permit free access to the cavity 35. The lobes 170a also may interact with the internal threads of the nose cap to help prevent the nose cap, sleeve and front spring from flying freely when disconnected from the barrel.

Second Exemplary Penetration Controller

Figure 15A:
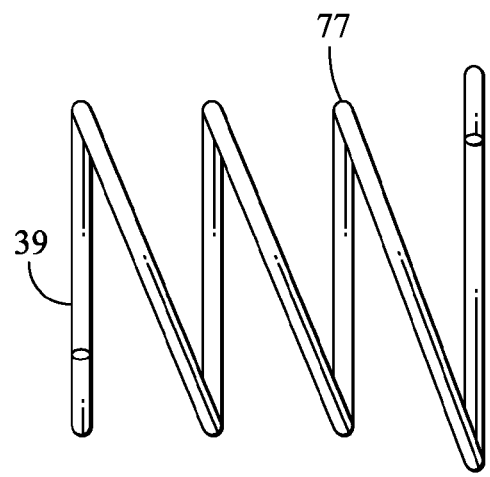
FIGS. 15A-15F are side views showing different compression spring penetration controls of various lengths and helical advance rates that affect needle penetration depth.
Figure 15B:
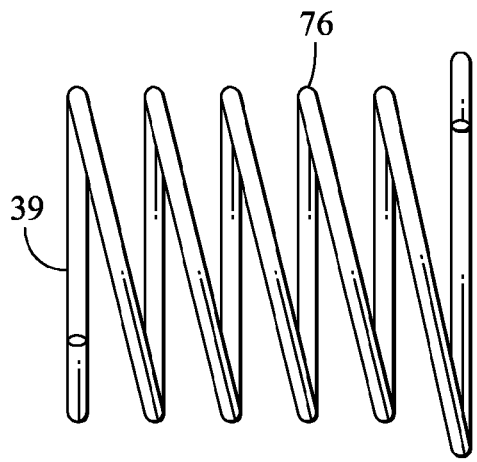
Figure 15C:
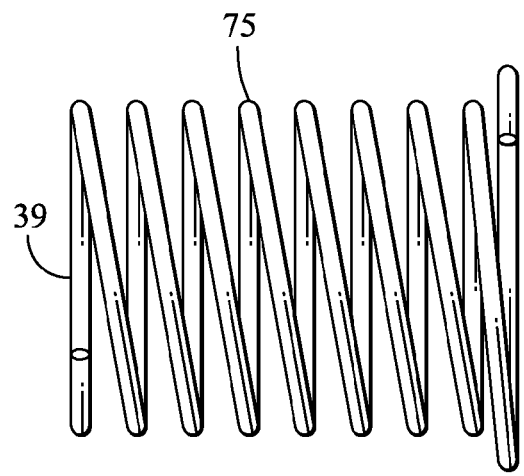

Another form of the penetration control may be provided in a form and construction which uses a selected spring of a particular fully compressed length dimension. FIGS. 15A-15C illustrate by way of example several springs 75, 76, 77 that will have different fully compressed lengths but similar lengths when installed in device 30. In each one of the springs, one of the spring ends will function as the abutment against which the needle hub engages or other parts engage as explained further below. The needle hub will stop when the spring is fully compressed and the desired penetration depth is attained.

By using a spring 75 that is selected for a desired compressed length, the spring itself becomes the penetration controller when fully compressed between the needle hub and the nose cap 45. Thus the spring can have dual functions: offering yieldable resistance to slow forward motion of the adjacent needle subassembly; and stopping such forward motion once the needle reaches the selected penetration depth and the spring becomes fully compressed.

The selected springs 75-77 can be made to fit frictionally within the nose cap 45 in order to keep the spring and nose cap together. This simplifies access to the cavity 35 and a needle assembly therein. It also mitigates flying discharge of the nose cap and spring when disconnected. Thus, the cap 45 and spring can be assembled so both can be simultaneously removed from the barrel as a unit. Changing from one spring to another to accommodate different penetration depths is a simple matter of removing the nose cap from the barrel and changing the spring. Alternatively, an assembly including a nose cap and different spring can be used to change penetration depth.

Figure 15D:
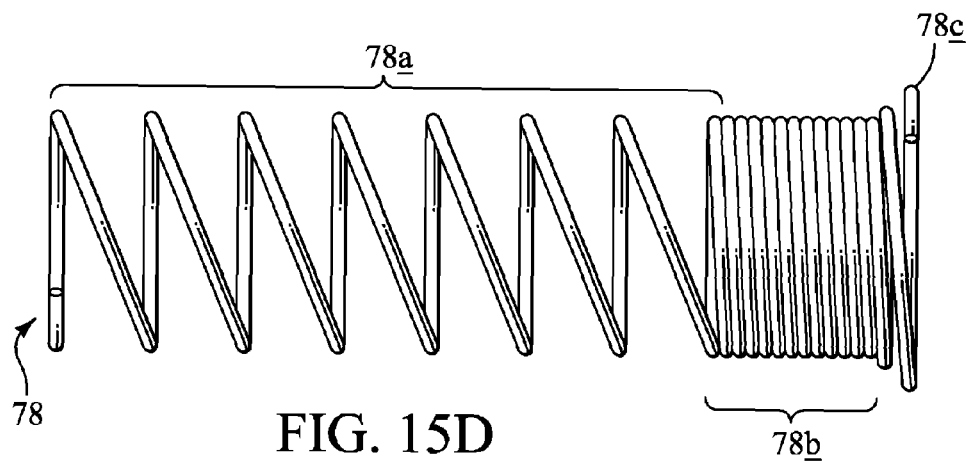
Figure 15E:
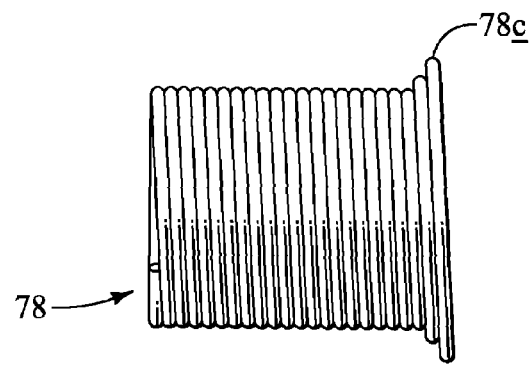
Figure 15F:
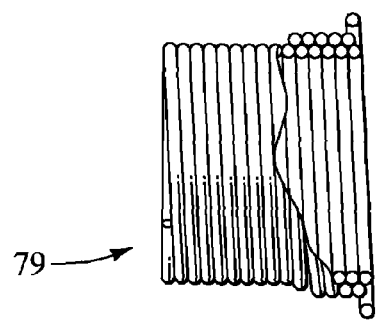

FIGS. 15D, 15E and 15F show additional novel concepts in using the forward spring for penetration control and absorption of energy from the moving drive and syringe assembly. FIG. 15D shows spring 78 in a free and uncompressed condition. Spring 78 has three sections, 78a, 78b and 78c. Section 78a has spaced helical or spiral windings which may be collapsed due to force applied by the driver through the syringe assembly. Section 78b includes one or more dead windings which are close or tight and are normally not compressible due to application of axial compressive force to spring 78. Section 78c is enlarged end coils or windings that are radially contracted when installed in the nose cap receptacle and serve to tie the spring and nose cap together.

By adjusting the relative proportion of sections 78a, 78b and 78c, the compression and energy absorption properties of the forward spring can be adjusted to provide different penetration control and different deceleration characteristics More dead coils reduce energy absorption as the forward spring is compressed because there are fewer active coils to absorb energy. Thus the increase in dead coils can be used to maintain adequate syringe power for injection and dispensing of the medication.

FIG. 15E shows spring 78 in a fully compressed but axially aligned and stacked condition. This occurs when the spring has stronger and/or large spring wire. The spring made with stronger wire will thus reach a fully compressed state and then relatively abruptly stop at the demonstrated penetration depth for that design of spring.

FIG. 15F shows a spring 79 similar to spring 78 with similar sections. Spring 79 does, however, demonstrate a different type of behavior upon full compression. The spring wire is made finer and less strong. This causes the spring to compress and then distort into a distorted collapsed condition. This condition provides a two-stage compression action. In the first stage or phase, the spring compresses in a typical or nearly typical stack arrangement. In the second stage or phase, the spring distorts with various windings being forced to radially change, thus distorting and collapsing with some winding either moving inside of other windings or overriding other windings. This construction effectively provides shock absorption and energy absorption capabilities that reduce shock after the spring has been fully compressed and allow energy absorption after full compression into a stacked array and helps or eliminates breakage of the syringe hub and other parts of the injector. It also provides cushioning as the syringe and driver decelerate to a stopped condition.

As examples, syringes made of wound or coiled music wire having wire diameter size of about 0.015 inch tend to collapse and distort as indicated in FIG. 15F. In comparison, springs wound from music wire having a diametrical size of 0.018 inch tend to remain in a stacked coil array as indicated in FIG. 15E.

These are current preferred wire sizes for injection devices using only a spring as the penetration control. Although such constructions are not as precise in demonstrating consistent penetration depth, they are sufficiently consistent for the administration of many medicines. They also are more economical to produce and eliminate the penetration control 38 having tubular sleeve 70 and flange 170 or other similar relatively inelastic penetration control elements. They are also less expensive to produce and assemble.

Use of finer spring wire has another beneficial effect. The springs tend to distort more easily and further reduce the risk that a nose cap and spring assembly fly away upon removal, such as when preparing for administration of a second or subsequent dose.

Syringe Assembly Front Spring Load Distribution, Guidance & Cushioning

FIGS. 24 and 25 show front portions of an injection device having many of the same features as described elsewhere herein. Description of the common features are made using the same reference numbers and the description which is common will not be repeated.

The embodiment of FIGS. 24 and 25 differ in that a load distribution ring 171 is provided to act in several capacities. The first capacity is to distribute the forces developed between the front spring 75 and the syringe, particularly at the syringe assembly hub 21. The second capacity is to act as a guide piece to help maintain the coaxial position of the syringe assembly hub within the barrel cavity. The third capacity is to also distribute and equalize force about the annular abutment 170 so that the forces developed against the syringe are not concentrated.

The ring 171 is preferably made about the same size as the barrel cavity portions within which the guide ring moves during operation of the injector. This is advantageously done by making the ring within a range of about −0.001 inch to about −0.004 inch compared to the adjacent barrel cavity interior diameter. Other size relationships are also believed operable.

Ring 171 is preferably made from a stainless steel or other suitable material which is strong and sufficiently stiff to help distribute the load evenly which is applied across the ring.

FIGS. 24 and 25 further show a resilient cushion in the form of a cushion or pad ring 172 which surrounds the syringe hub 90. The cushion is preferably made from an elastomer material such as natural rubber or Santoprene 8281-45-med having a durometer value of about 45. In the uncompressed state the cushioning pad ring 172 is about 0.030 inch smaller in diameter than the load distribution and guide piece 171. This allows the pad ring to expand outwardly in a radial direction when load is applied thereto as the syringe is driven against the front spring and resistance is developed in association with dispensing the fluid medication from the front needle. An outer diameter which is larger and closer to the adjacent barrel internal diameter may lead to lateral strain that causes the pad ring 172 to develop frictional drag against the barrel bore. This in turn requires more driver force to be provided in order to overcome the friction and creates added stress and strain on the syringe and other parts of the injector.

FIGS. 26 and 27 show another embodiment similar to that shown in FIGS. 24 and 25. The embodiment of FIGS. 26 and 27 is not provided with a load distributor and guide ring like ring 171 of FIGS. 24 and 25. Instead, the cushion pad 172 directly bears on the syringe hub and the front spring. Although this construction is not as preferred as that shown in FIGS. 24 and 25, it is believed operable. Due to the less uniform load application a harder and more durable elastomer material may be needed to allow repeated use of an injector so constructed.

In either of the constructions shown in FIGS. 24-27, the cushion pad 172 has been found to be superior at moderating forces experienced by the syringe hub 90 and thus reduces the risks of failure or breakage of the hub or other portions of the syringe assembly.

Summary of Front Return Spring Functions

The front or return spring thus performs a number of important functions. It maintains the syringe assembly in a retracted position prior to use, such as during handling, shipping, carrying by the user and other situations. Any one of these may by routine or accident cause force to be developed on the syringe and return spring. The return spring thus maintains or helps to maintain the syringe in a retracted position prior to firing but does so in a manner that absorbs shock and minimizes the risk of syringe ampule breakage.

The return springs also serves to help keep the injection needle up inside the nose cap or barrel to keep it in a hidden position to prevent user alarm at sight of the needle.

Another function of the return spring is to counteract against the drive spring upon triggering of the injection. The drive spring accelerates the syringe down the barrel and the kinetic and well as stored spring energy is preferably dissipated to prevent or reduce the risk of syringe ampule breakage or breakage of other components of the forward end of the injector which in one way or another must take the force and dissipate the energy. Dissipation of energy is particularly enhanced when the spring deforms as illustrated in FIG. 15F.

Another important aspect of the forward or return spring is in some embodiments to provide for proper insertion of the seal insertion needle 22 into and through the ampule seal 23. This is accomplished by selecting a return spring which develops the return force needed to cause seating of the ampule and insertion of needle 22 at or slightly before final penetration depth is achieved. Thus, the spring may provide for delayed administration of the medicine until the needle penetration depth is proper.

In some forms of the inventions the front or return spring may by itself serve as the penetration control. This simplifies the construction of the injector and saves costs where the required consistency of penetration control for the medicine being used is within the demonstrated consistency of the penetration controller spring being used is satisfactory. Where these parameters are met the more complex penetration control sleeve can be eliminated.

A still further advantageous function of the front return spring is to hold or help hold the spring with the nose cap. This is accomplished in the illustrated embodiments by using a spring which has enlarged coils toward the forward end. These larger coils serve to maintain the spring with the nose cap when the nose cap is removed. This may prevent or minimize any risk of the nose cap and spring flying off. This property of retaining the spring and nose cap also simplifies handling the nose cap by keeping the nose cap, spring and any tubular penetration control together as a cap and penetration control assembly.

Thus it can be seen that the front return spring performs a surprising number of different functions and advantages or combination of different functions and combinations of advantages.

Considerations for Double Needle Syringe Subassembly

Description to this point has been generic with respect to the different needle subassemblies 10, 11 because both needle forms can be utilized with the structure described. With respect to the double needle subassemblies, however, the penetration depth controller 38 and the syringe driver 36 are configured to perform an additional function of penetrating the seal 23 using penetrating needle 22.

The seal penetrating task is accomplished as the triggered syringe driver 36 forces the needle subassembly forwardly. As the subassembly 11 moves forwardly, the hub 21 slides into abutment with the syringe abutment surface 39 of the penetration controller. Continued applied force will cause the associated ampule 12 to slide on forwardly although the hub 21 and needles 22 will remain axially stationary in relation to the abutment 39. The forward moving ampule will thus be penetrated by the rearwardly projecting needle 22.

It should be appreciated that tissue penetration depth is not derogatorily affected by the ampule piercing operation. The forward needle 24 will move toward the selected penetration depth as the hub 21 moves to engage the abutment surface 39. Continued forward force against the syringe subassembly by the driver 36 will cause the injection needle 24 to continue being extended as the rearward needle 22 penetrates seal 23. Hub 21 is thus seated as full penetration of the forward needle 24 occurs. Further movement of the driver causes the ampule medication to be dispensed and injected.

The double needle subassembly 11 may in some cases be preferable to the open communication single needle subassembly 10. This can be visualized in that the injection needle will be fully or almost fully penetrated into the flesh before the injected medicine is dispensed into the flesh. With the single needle syringe there is a potential effect of putting medication above the final needle injection depth. So in actual operation the double ended needle may provide more controlled and/or reproducible dispensing of the medicine at the final needle depth. This is what is done in the hospital setting with a manual injection in that the doctor or nurse first places the needle to the desired depth and then presses the plunger. It also prevents loss of medicine as the injection needle passes through intermediate tissue.

The wire diameters for some return springs are suitable for achieving the seating and desired insertion of the ampule by needle 22 at the same time the injection needles reach their desired final penetration depth. This is caused by the springs either being weak enough (lower spring rate) so that the penetration control sleeve 38 performs the final seating and insertion of needle 22 through seal 23. In other embodiments, such as when the penetration control is solely by the spring, the spring rate of the return spring is selected to similarly provide for seating and insertion of needle 22 through seal 23 also at or near the desired final penetration depth. In either case, this provides proper administration into the tissues which are the intended tissue for the desired final penetration depth.

The injector also performs another important novel function when used with double needle syringe assemblies, such as 11. Such assemblies require the needle assembly to be seated manually or with a device holder before performing manual injections. The action of firing the injector carrying a double needle syringe causes the needle assembly to seat or mate with the sealed ampule. Thus a manually useful syringe is automatically formed. This indicates the multiple functions provided by injectors described herein. One function is to automatically administer the first dose. Another function is to seat the double needle syringe assembly with the sealed ampule to form a manually administrable syringe from a dual needle syringe and sealed ampule. A further function is to provide a reliable backup syringe for situations where the syringe may be misused and the second dose is the only dose and can be administered manually for ultimate reliability as may be dictated by difficult situations on the battle field or in other situations.

Storage and Carrying Case

FIGS. 28-36 show a preferred outer or carrying case in which the injectors described herein may be carried in a protected manner. FIG. 28 shows that the preferred carrying case 200 has a lower or bottom part 201 and an upper or top part 202. The upper and lower parts are joined by a detachable joint used to keep the parts together until such time as an injector, such as injector 30, is needed and can be removed from the carrying case. Before explaining the operation of the carrying case, a detailed explanation of the features thereof will now be given.

Carrying case 200 is designed to carry an injector with the driver and trigger end of the injector inserted into the upper case part 202. The muzzle and needle end of the injector is inserted into the lower case part 201.

In the preferred construction shown, a bottom end receptacle 205 receives the muzzle end of the injector. This is preferably done so that the sheath remover front wall 82 bears upon a support ledge 206. Ledge 206 is preferably padded with an annular pad 209. This construction prevents loading of the exposed needle sheath to forces that develop during movement, handling and mishandling (such as dropping) of the carrying case with injector supported therein.

The length between ledge 206 and the upper end of the case top piece 202 is nearly equal but shorter than to the length of the injector between the safety cap or other top end piece and the face surface 82 of the sheath remover. This construction advantageously provides a small amount of clearance so that the injector is not loaded in an axial manner when stored in the carrying case.

FIG. 28 shows that the upper part 202 of the carrying case is advantageously provided with a clip mount 206 which can be welded to the upper part 202 or integrally formed therewith during molding of the upper part. The clip mount is used to mount a clip 207 which is similar to a clip on a pen. The clip is preferably made of metal having spring properties that hold the clip end 208 against the upper case piece 202. The clip may be used to help hold the carrying case in a user's pocket or in luggage, brief cases, cosmetic bags or in or on other parts of a user's garments or accouterments.

FIGS. 34 and 35 show the clip mount 206 in greater detail. Other configurations are also possible. In any design the mount is preferably durable and prevents the clip 207 or mount 206 from being broken from the carrying case upper part 202.

FIG. 28 shows that the upper and lower case parts are preferably constructed so as to form a detachable joint 210. Although a threaded joint is acceptable, it has been found more preferable to have a joint which can be easily and quickly disconnected so that in an emergency the injector can be accessed quickly to administer a medicine without delay. In the construction shown, the bottom part 201 includes an insertion part 220 (FIG. 29) which is sized and shaped to fit within an insertion receptacle 230 (FIG. 36) formed on the open complementary end of the upper case part 202. Insertion section 220 is advantageously provided with a retainer projection or projections 221 which are received within an annular recess 231 (FIG. 36) to provide a catch or mating engagement which retains the two case parts together until needed by a user.

The connection joint 210 is also advantageously provided with quick release which can be provided in the form of two projections 241 which are received in complementary receptacles formed on the mating part 201. The projections are preferably semicircular to mate into semicircular receptacles 242 adjacent to the insertion part 220. This configuration allows the case to be easily opened by twisting the two case parts 201 and 202 relative to each other only a relatively small angular displacement. The semicircular projections and receptacles thus interact to cam the two case parts away from one another and dislodge the retainer projections 221 from the annular recess 231. Thus, by merely twisting the two case parts less than about 1/10th of a rotation, the carrying case is opened and the injector contained therein may be easily removed.

FIG. 36 also shows a shoulder 232 which is recessed an amount so that the insertion section 220 extends into the joint receptacle bringing the end surface of the insertion part into engagement with the shoulder 232. This also facilitates proper extension of the insertion part into the receptacle so that the projections 221 properly fit into the annular groove 231.

Sharps Disposal

The novel constructions shown herein are also advantageous in that they are adapted to provide a sharps container or containers for holding the syringe assembly after the medicine has been injected. In one form the syringe assembly is removed or withdrawn from the injector through the muzzle end without a needle sheath thereon. The return spring and related parts forward of the syringe assembly are also removed. With the needle end of the syringe first, the syringe is then inserted into the barrel cavity in reverse orientation. The nose cap 45 without return spring and any penetration control sleeve is then connected or attached to the barrel to secure the syringe therein for safe handling and proper disposal.

In another form the syringe assembly is inserted into the carrying case and the two parts of the carrying case are rejoined. The carrying case acts as a portable sharps container. Thus the invention may also provide a safe means for carrying the syringe and associated needle or needles to a larger sharps disposal container for shipping and disposal. It may also be placed in the carrying case to provide a combination which is extremely resistant to breakage and needle exposure.

Added Methods and Operation

In addition to the various descriptions given elsewhere herein concerning methods and operation of the inventive components, the following added explanation is provided to supplement the description.

A method aspect according to the present invention is provided for driving a syringe needle 24 or 17 to a selected penetration depth. Aspects of the method will be discussed along with a description of operation and use of the invention.

The process initially includes placing the injector in a cocked position. This is preferably done during manufacture. The injector is cocked with the safety cap 55 removed and pressing the driver bar 37 rearwardly. The barbs 54 on the driver shaft are moving and then extending into hole 60 at the trigger end of firing sleeve 57. This performs a compressing of the drive spring 50 and catching of the barbs 54 upon annular piece 43. Once the device is cocked, the safety cap 55 can be installed to prevent accidental firing of the driver. This action places the pin 56 between the barbed legs of the driver bar 37. Pin 56 prevents the barbed ends from moving toward one another and releasing the driver bar or shaft. This readies the apparatus for reception of the selected syringe assembly.

Then the process involves selecting a suitable syringe subassembly. The selecting involves syringes having the desired fluid volume, injection needle length and durability for the intended purposes. In preparation for installation of the syringe subassembly, the plunger rod 62 may be attached to the syringe plunger 14, which allows for performance of a step in which at least one stop collar 64 may be attached to the plunger rod 61 for dosage control if the syringe is provided with a multiple dose charge. If the plunger rod 61 can be adjusted for axial length, then adjusting the plunger rod occurs at this time to provide a desired or consistent discharge volume or dose. Thus a step of determining a dosage to be dispensed from the apparatus is accomplished. Once adjusting and/or determining step has been completed, the dose setting step is complete.

Further preferred methods include inserting a selected syringe subassembly through the open forward end of barrel 31. The methods further include locating and installing the syringe subassembly to a desired position within the interior of barrel 31. This is accomplished with the nose cap 45 removed and by sliding the selected syringe subassembly with the open end 13 first, into the barrel cavity.

The above steps and procedures according to the inventions may in general be accomplished with either the fixed needle or double needle syringe subassemblies 10 or 11.

Further processes according to the invention may also include adjusting penetration depth. Adjusting penetration may be accomplished by selecting a desired penetration controller 38, spring penetration control or other penetration control, having a length which positions the abutment surface 39 at a desired location. This may include a selectable number of penetration stop positions. This can be accomplished while the nose cap 45 is separated from the barrel 31 either by placing a selected length of penetration control sleeve 38 into the nose cap, or by placing a selected penetration control spring 75-79 into the nose cap. A combination of control spring and fixed control element may also be possible.

In the example illustrated in FIGS. 3-6, the sleeve type penetration controller 38 is used, and is frictionally positioned within the cap to abut the nose cap interior front wall adjacent the needle aperture 34. Return spring 71 is also placed within sleeve 70, prior to installing the controller and spring subassembly into the nose cap interior cavity. This is preferably done with the enlarged end of the spring engaging the front, flanged end 170 of sleeve 38.

The spring, penetration controller and nose cap assembly can then be installed to the barrel. This is advantageously done in the illustrated embodiments by threading the nose cap onto the barrel until the stop shoulder 47 is engaged by the rearward end of the nose cap, to assure proper axial spacing between the syringe abutment surface 39 and the syringe hub. The return spring may be made to abut a ring-shaped stainless steel guide and load distributor 171 (FIGS. 24 and 25) to help assure accurate firing and less decelerated stopping of the syringe subassembly.

Alternatively, a spring of selected compression length (for example, one of the springs 75-79), can be used to determine penetration depth. In this aspect, a spring is selected that has a compressed axial length related to a desired needle penetration depth. The selected spring is then mounted to the nose cap 45, such as by frictionally sliding the spring into place within the cap and/or along with the guide 171. Now the end of the spring facing the syringe hub becomes the syringe abutment surface and the penetration depth will be gauged by the fully compressed length of the spring. The spring may have various number of active coils and in some designs dead coils to help provide desired penetration with sufficient energy for penetration. Once the selected spring is mounted within the nose cap, the assembly can be threaded onto the barrel to a point where the stop shoulder 47 is engaged.

The sheath remover 80, if not already in position on the nose cap 45, can be slid into position on the nose cap 45, to position the sheath engaging fingers 82 over the sheath. The fingers will perform by flexing, thereby allowing the sheath remover to act by sliding over the extent of the needle sheath 19 that is exposed forwardly of the nose cap 45.

Once the nose cap 45 and sheath remover 80 are in place and the safety 55 is attached, the device is loaded, cocked and in a safe condition nearly ready for use. The device can be safely carried or stored in this condition until such time that an injection is to be administered.

The following discussion will describe a single dose use, and a double dose use of the illustrated and other auto-injectors according to the invention. The described uses are both possible using the same or similar procedures with both a single fixed needle syringe subassembly 10, or the double needle subassembly 11.

Prior to injection, the user can remove the protective sheath 19 from the needle subassembly by moving, such as by sliding, the sheath remover 80 forwardly. This performs a disengaging step, freeing the sheath remover from the nose cap 45. The sheath remover fingers 82 perform by engaging and catching or binding against the sheath lip 89. Further removal of the sheath remover applies axial forces upon the sheath that act by pulling the sheath outwardly through the needle aperture 34 in the nose cap 45. The sheath remover thus performs an action of removing the sheath from the syringe assembly and other parts of the auto-injector.

The user may perform a removing step to remove the safety 55 from the opposite end of the barrel. This is advantageously done by pulling the safety and attached safety pin 56 from between the barbed legs of the driver bar 37 or other driver shaft assembly. This arming step involves removing or disabling the safety, thus readying the injection device for dose administration.

To perform injecting, the user presses the nose cap against the tissue area to be injected. The pressing action causes movement of the firing sleeve 57 forwardly relative to the barrel. The barbs on the driver bar or shaft assembly will move toward one another collapsing inwardly by engaging the barbs against the walls of opening 60. This action releases the driver bar, which is now allowed to move forwardly, such as by sliding, in response to force applied by the driver. This forcing of the driver shaft serves to free the driver release into a driving action wherein the driver bar moves forward and acts by engaging the plunger rod. The driving action also forces the needle subassembly forward. This acts by penetrating the adjacent tissue of the user with the needle and also serves by penetrating any second needle through the seal of the ampule.

As the needle subassembly moves forwardly, the return spring 71 or selected penetration control springs 75-79 are acted upon to perform a compressing of the forward spring. The spring, nose cap and any penetration control acts by restraining and stopping the forwardly moving needle hub. In arrangements in which the engaged end of the return spring also constitutes the syringe abutment surface, the selected spring will fully compress at a preselected axial location, stopping needle penetration at the desired penetration depth. The same penetration depth can be effected in arrangements in which the return spring 71 compresses to a point where the needle hub engages the fixed abutment surface 39 on the selected sleeve type penetration controller 70. Penetration depth is determined by the selected axial position of the abutment surface, whether it be on a penetration control sleeve or by fully collapsing a spring having a desired fully compressed length.

Once the abutment surface or full spring compression point is reached, the drive spring 50 will continue pushing the plunger rod forwardly, dispensing medicine. In instances where a single needle syringe subassembly 10 is used, continued forward motion of the plunger will result in injection of the medication. Medication is also injected when a double needle assembly 11 is provided within the barrel 31, but after the ampule is driven forward onto the seal penetrating needle 22.

Medication will be injected as the spring 36 performs by forcing the plunger forwardly. Such forcing continues until such time that the plunger shaft engagement head engages any desired stop collar 64 or stack of stop collars. This marks the end of the injection, and the prescribed dosage amount will have been injected at the selected injection penetration depth. The device is now ready for either recocking and reloading with another syringe subassembly, or for preparation to inject a second dose or subsequent doses of medication which are still within the ampule due to stopping action performed by one or more stop collars 64.

The penetration depth and the dosage amount are controllable as discussed above. This is advantageously done by provision of the removable or adjustable stop arrangements within the barrel 31. The dosage can be selectively controlled by the stop collar 64 and the adjustable length plunger rod 61.

Penetration depth can be controlled by selecting the axial position at which the needle hub is stopped within the barrel 31 as a function of the selected or adjusted penetration control, such as by penetration controller 38 or the collapsed condition of a penetration control spring.

The novel methods may also include administering a second injection. According to some forms of the invention, this can be done with the same syringe assembly. Alternatively it may be done using a second or subsequent syringe assembly. When using a single syringe, the user performs by removing the nose cap 45 and sliding or extracting the syringe assembly from the barrel cavity. Any stop collar 64, collars or portions thereof can then be removed, such as by laterally removing the collar, collars or portions thereof from the plunger rod, thereby allowing the plunger to be pushed further forward within the ampule to inject another dose. This is preferably used to administer a second dose in a manual mode of operation.

If the injector is to be used for administering the second dose, then the injector is recocked by removing the syringe assembly and then holding the barrel and depressing the driver using a screw driver or other tool which is extended into contact with the driver bar or shaft 37.

The safety, such as safety cap 55, can now be placed back over the rearward end of the device. This safety placing action causes inserting of safety pin 56 wherein the driver bar legs form a safety opening receiving the safety pin 56. The installed safety pin performs by holding them apart and rendering the device into a safe condition, thereby avoiding unintentional firing.

When the syringe subassembly 10 or 11 is received back in the barrel (such as with stop collar 64 removed), the ampule will slide back further into the barrel until it abuts with the spring guide sleeve 33 (FIG. 8). The subassembly will be held in this position by the spring 71 (or by the selected other springs 75-79) as the nose cap 45 is replaced. Replacement of the nose cap completes the needed steps for a second or subsequent use of the device to deliver a second auto-injected dose. If the injection is to be given immediately, there is no need to replace the sheath and sheath remover. However if the second injection is to be delayed for a time, it is possible for the sheath 19 and sheath remover 80 to be re-installed even though the needle is now carried safely within the nose cap. Alternatively, the sheath and sheath remover are not reinstalled to reduce risks of injury or contamination.

Administration of the second dose may be accomplished automatically in the same manner as described above. In such operation the driver will function to depress the plunger through the axial distance previously occupied by the stop collar 64.

The injection apparatuses according to this invention may also allow the administering of a second or subsequent dose in a manual manner. In such alternative mode of operation the syringe assembly is removed from the barrel in a manner the same as or similar to that described above. If the initial dose does not work with sufficient effectiveness, then the user may manually insert the forward needle into the flesh of the patient and depress the plunger rod with the thumb. This procedure may be used when recocking the driver is difficult or impossible, or to speed administration of the second or subsequent doses.

More than one stop collar can be provided, and more than two injections from the same syringe may be administered. It is also noted that the injection device may be provided without a stop collar, so the syringe would be used only for one auto-injection. Excess medicine can be provided in the syringe for manual administration. Dosage amounts can be more accurately determined by axially adjusting the headed part 62 of the plunger rod 61. In either case, the device can be re-used. In a first mode of operation, the device can be reset by recocking and installing the same syringe previously used. In a second mode of operation, the device can be reset in the manner described above and a second syringe subassembly can be installed and used and operated as done with the first syringe.

Manner of Making

Many of the components of the auto-injector are preferably made by molding, such as injection molding, a suitable medical grade transparent plastic into the configurations shown and described herein. Metal pieces are turned or fabricated according to various well-known metal working techniques. Preferred components for the injector are detailed below or stated above.

The plunger shaft 63 is preferably made from a metal material, such as 2024 grade aluminum which is anodized with a clear material per military specification MIL A 8625 C clear.

The tubular penetration control sleeve is preferably made from a suitable plastic material which is molded into the desired shape and size. A preferred material is sold under the name Celcon TX90 Plus. Others are possible such as Nylon 6 (Capron 8253), or M270 Celcon.

The springs are preferably made from steel music wire having high strength for the small size and excellent spring retention capabilities. The return spring may vary, but in some forms 0.015 inch diameter has been preferred, type 16 A228; however, heavier wire may be preferred in various constructions. The drive spring is preferably ASTM-A313 type 17-7 PH stainless steel wire, 0.033 inch diameter.

The driver release annular piece 43 is preferably made from a suitable steel, such as 12L14 Grade A steel, which is preferably zinc plated per ASTM B633-85 Type III SEI.

The nose cap, safety cap piece and sheath remover are preferably made from a molded plastic such as Amoco #4039 polypropylene or Polymerland #1120.

The needle sheath is preferably made from high density polyethylene Spec. #MS-4079.

The carrying case is preferably made from a non-transparent or opaque colored plastic material, such as polypropylene, for example, Rexene #17C9A polypropylene.

The spring clip on the carrying case is preferably made from a suitable steel, such as a chrome or other plated steel which does not easily rust, or from a suitable stainless steel, such as 0.010 inch 301 stainless steel half hardness with #2 finish.

The sheath remover and safety cap are preferably made from DuPont Zytel 101L.

The firing sleeve and plunger adjustment screw are preferably made of Bayer Markrolon #2607-1112 polycarbonate.

The drive spring bushing is preferably made from Amoco #4039 polypropylene.

The barrel is preferably made from Plexiglass DR 101 Acrylic. The spring guide for the drive spring is preferably made from Dow 478-27-W high impact polystyrene.

The stop collar and bushing edge against which it bears are preferably made from Amoco #4039 polypropylene or Polymerland #1120.

The spring release is preferably made from 8 NOS high density 70/30 brass CL C2600 per ASTM B36-91A.

Further Aspects and Features

The above description has set out various features and aspects of the inventions and the preferred embodiments thereof. Such aspects and features may further be defined according to the following which may individually or in various combinations of the recited features help to define the inventions in accordance herewith.

An apparatus forming a medicine injection device comprising a barrel having a muzzle end with a needle receiving aperture, a syringe subassembly receiving cavity situated along the barrel adjacent the muzzle end, adapted to releasably and slidably receive a syringe subassembly for movement toward and away from the muzzle end with a needle of the syringe subassembly being capable of projection through the needle receiving aperture, a syringe driver connected to the barrel, and having a driver bar movable toward the muzzle end through the syringe subassembly receiving cavity, and a penetration controller mounted at the muzzle end of the barrel and having a syringe subassembly abutment spaced from the muzzle end to achieve a desired needle penetration depth position.

An apparatus forming a medicine injection device comprising a barrel having a muzzle end with a needle receiving aperture, a syringe subassembly receiving cavity situated along the barrel adjacent the muzzle end, adapted to releasably and slidably receive a syringe subassembly for movement toward and away from the muzzle end with a needle of the syringe subassembly being capable of projection through the needle receiving aperture, a syringe driver connected to the barrel, and having a driver bar movable toward the muzzle end through the syringe subassembly receiving cavity, and a penetration controller mounted at the muzzle end of the barrel and having a syringe subassembly abutment spaced from the muzzle end to achieve a desired needle penetration depth position, and further comprising a nose cap at the muzzle end of the barrel, and wherein the penetration controller is mounted using the nose cap.

An apparatus forming a medicine injection device comprising a barrel having a muzzle end with a needle receiving aperture, a syringe subassembly receiving cavity situated along the barrel adjacent the muzzle end, adapted to releasably and slidably receive a syringe subassembly for movement toward and away from the muzzle end with a needle of the syringe subassembly being capable of projection through the needle receiving aperture, a syringe driver connected to the barrel, and having a driver bar movable toward the muzzle end through the syringe subassembly receiving cavity, and a penetration controller mounted at the muzzle end of the barrel and having a syringe subassembly abutment spaced from the muzzle end to achieve a desired needle penetration depth position, and further comprising a sheath remover, releasably mounted on the barrel at the muzzle end for removing a needle sheath which covers at least part of said needle.

An apparatus forming a medicine injection device comprising a barrel having a muzzle end with a needle receiving aperture, a syringe subassembly receiving cavity situated along the barrel adjacent the muzzle end, adapted to releasably and slidably receive a syringe subassembly for movement toward and away from the muzzle end with a needle of the syringe subassembly being capable of projection through the needle receiving aperture, a syringe driver connected to the barrel, and having a driver bar movable toward the muzzle end through the syringe subassembly receiving cavity, and a penetration controller mounted at the muzzle end of the barrel and having a syringe subassembly abutment spaced from the muzzle end to achieve a desired needle penetration depth position, wherein the penetration controller comprises a sleeve and a resilient pad which is positioned between the syringe subassembly and the penetration controller.

An apparatus forming a medicine injection device comprising a barrel having a muzzle end with a needle receiving aperture, a syringe subassembly receiving cavity situated along the barrel adjacent the muzzle end, adapted to releasably and slidably receive a syringe subassembly for movement toward and away from the muzzle end with a needle of the syringe subassembly being capable of projection through the needle receiving aperture, a syringe driver connected to the barrel, and having a driver bar movable toward the muzzle end through the syringe subassembly receiving cavity, and a penetration controller mounted at the muzzle end of the barrel and having a syringe subassembly abutment spaced from the muzzle end to achieve a desired needle penetration depth position, and further comprising: a nose cap releasably mounted to the barrel, and wherein the penetration controller is spring mounted to the nose cap and having a compressed length which controls penetration depth of the needle which extends from the muzzle end.

An apparatus forming a medicine injection device comprising a barrel having a muzzle end with a needle receiving aperture, a syringe subassembly receiving cavity situated along the barrel adjacent the muzzle end, adapted to releasably and slidably receive a syringe subassembly for movement toward and away from the muzzle end with a needle of the syringe subassembly being capable of projection through the needle receiving aperture, a syringe driver connected to the barrel, and having a driver bar movable toward the muzzle end through the syringe subassembly receiving cavity, and a penetration controller mounted at the muzzle end of the barrel and having a syringe subassembly abutment spaced from the muzzle end to achieve a desired needle penetration depth position, and further comprising a dose stop collar releasably mounted within the barrel to stop movement of the driver bar toward the muzzle end.

An apparatus forming a medicine injection device comprising a barrel having a muzzle end with a needle receiving aperture, a syringe subassembly receiving cavity situated along the barrel adjacent the muzzle end, adapted to releasably and slidably receive a syringe subassembly for movement toward and away from the muzzle end with a needle of the syringe subassembly being capable of projection through the needle receiving aperture, a syringe driver connected to the barrel, and having a driver bar movable toward the muzzle end through the syringe subassembly receiving cavity, and a penetration controller mounted at the muzzle end of the barrel and having a syringe subassembly abutment spaced from the muzzle end to achieve a desired needle penetration depth position, and further comprising a nose cap removably mounted to the barrel at the muzzle end and wherein the penetration controller is comprised of a penetration control sleeve with a needle hub abutment surface spaced a desired distance from the muzzle end.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected, wherein the penetration control includes a penetration control element within the barrel, having an abutment surface thereon.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected, wherein the penetration control includes plural penetration control elements which can be interchangeably used depending on the desired penetration depth for the dose of medicine to be dispensed.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected, and further comprising a resilient pad positioned between the double needle syringe subassembly and said penetration control to distribute forces experienced by the double needle syringe assembly when deployed into a fully extended penetration stop position.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected, wherein the penetration control includes a spring mounted within the barrel between the double needle and the muzzle end.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected, wherein the penetration control is comprised of a compression spring mounted to engage with a nose cap which is releasably secured to the barrel at the muzzle end.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected, and further comprising a nose cap removably mounted to the barrel at the muzzle end and defining the needle receiving aperture, and wherein the penetration control includes a compression spring mounted within the nose cap.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected, and further comprising a nose cap removably mounted to the barrel and defining the needle receiving aperture, and wherein the penetration control includes a sleeve positioned at least partially within the nose cap and having an abutment surface for abutment with the double needle syringe subassembly.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected, wherein the flesh penetration needle is covered by a sheath; and further comprising a sheath remover releasably mounted on the barrel at the muzzle end and including a needle sheath gripper for engaging and removing the sheath.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected, wherein the syringe driver includes a driver bar slidably positioned within the barrel, and wherein the double needle syringe subassembly has a plunger rod of adjustable axial length.

An apparatus forming a medicine injection device comprising a barrel having a muzzle end with a needle receiving aperture, a syringe subassembly cavity within the barrel, a double needle syringe subassembly within the barrel and sized to slide within said cavity, the double needle syringe subassembly having at least one fluid medication receiving ampule with a rearward end slidably receiving a plunger piston and a forward end having a penetrable seal, a double needle mounted adjacent the penetrable seal, the double needle having a seal penetration needle projecting rearwardly toward the seal and a flesh penetration needle projecting forwardly for deployment through the needle receiving aperture, a syringe driver on the barrel, and having an driver bar movable to operatively engage the syringe subassembly, to move the syringe subassembly toward the muzzle end through the syringe subassembly cavity, and a penetration control which controls penetration of the flesh penetration needle to a depth stop position to provide a desired final penetration depth which can be varied by choice of the penetration control selected, wherein the syringe driver includes a driver bar which engages a plunger rod of the double needle syringe subassembly, and a removable dosage stop attached to the plunger rod to limit motion of the driver bar in a forward direction toward the muzzle end.

An apparatus forming a medicine injection device, comprising a barrel having a muzzle end with a needle receiving aperture, a syringe subassembly receiving cavity along the barrel, a syringe subassembly within the barrel and sized to slide within the cavity, the syringe subassembly having an ampule for housing fluid medication, a needle, and a plunger for forcing the fluid medication from the ampule through the needle, a driver for forcing the syringe subassembly to penetrate flesh and displace fluid medication through the needle, the driver being movable between a cocked position and extended positions, a driver release for controllably releasing the driver from the cocked position to move toward said extended positions, a removable stop within the barrel for halting movement of the driver at a selected extended position, and a penetration control which can be varied and having an abutment surface which stops movement of the syringe subassembly such that the needle projects from the muzzle end a desired penetration distance.

An apparatus forming a medicine injection device, comprising a barrel having a muzzle end with a needle receiving aperture, a syringe subassembly receiving cavity along the barrel, a syringe subassembly within the barrel and sized to slide within the cavity, the syringe subassembly having an ampule for housing fluid medication, a needle, and a plunger for forcing the fluid medication from the ampule through the needle, a driver for forcing the syringe subassembly to penetrate flesh and displace fluid medication through the needle, the driver being movable between a cocked position and extended positions, a driver release for controllably releasing the driver from the cocked position to move toward said extended positions, a removable stop within the barrel for halting movement of the driver at a selected extended position, and a penetration control which can be varied and having an abutment surface which stops movement of the syringe subassembly such that the needle projects from the muzzle end a desired penetration distance, and further comprising an adjustable length plunger shaft.

An apparatus forming a medicine injection device, comprising a barrel having a muzzle end with a needle receiving aperture, a syringe subassembly receiving cavity along the barrel, a syringe subassembly within the barrel and sized to slide within the cavity, the syringe subassembly having an ampule for housing fluid medication, a needle, and a plunger for forcing the fluid medication from the ampule through the needle, a driver for forcing the syringe subassembly to penetrate flesh and displace fluid medication through the needle, the driver being movable between a cocked position and extended positions, a driver release for controllably releasing the driver from the cocked position to move toward said extended positions, a removable stop within the barrel for halting movement of the driver at a selected extended position, and a penetration control which can be varied and having an abutment surface which stops movement of the syringe subassembly such that the needle projects from the muzzle end a desired penetration distance, wherein said abutment surface is a surface on a penetration controller of a selected length.

An apparatus forming a medicine injection device, comprising a barrel having a muzzle end with a needle receiving aperture, a syringe subassembly receiving cavity along the barrel, a syringe subassembly within the barrel and sized to slide within the cavity, the syringe subassembly having an ampule for housing fluid medication, a needle, and a plunger for forcing the fluid medication from the ampule through the needle, a driver for forcing the syringe subassembly to penetrate flesh and displace fluid medication through the needle, the driver being movable between a cocked position and extended positions, a driver release for controllably releasing the driver from the cocked position to move toward said extended positions, a removable stop within the barrel for halting movement of the driver at a selected extended position, and a penetration control which can be varied and having an abutment surface which stops movement of the syringe subassembly such that the needle projects from the muzzle end a desired penetration distance, wherein the penetration control is a compression spring that collapses to stop movement of the syringe subassembly.

An apparatus forming a medicine injection device, comprising a barrel having a muzzle end with a needle receiving aperture, a syringe subassembly receiving cavity along the barrel, a syringe subassembly within the barrel and sized to slide within the cavity, the syringe subassembly having an ampule for housing fluid medication, a needle, and a plunger for forcing the fluid medication from the ampule through the needle, a driver for forcing the syringe subassembly to penetrate flesh and displace fluid medication through the needle, the driver being movable between a cocked position and extended positions, a driver release for controllably releasing the driver from the cocked position to move toward said extended positions, a removable stop within the barrel for halting movement of the driver at a selected extended position, and a penetration control which can be varied and having an abutment surface which stops movement of the syringe subassembly such that the needle projects from the muzzle end a desired penetration distance, wherein the penetration control is comprised of a sleeve having a selected length dimension and a syringe subassembly abutment surface at a rearward end thereof, and further comprising a nose cap mounting the sleeve, and wherein the nose cap is releasably connected to the barrel at the muzzle end to allow installation and removal of the syringe subassembly.

An apparatus forming a medicine injection device, comprising a barrel having a muzzle end with a needle receiving aperture, a syringe subassembly receiving cavity along the barrel, a syringe subassembly within the barrel and sized to slide within the cavity, the syringe subassembly having an ampule for housing fluid medication, a needle, and a plunger for forcing the fluid medication from the ampule through the needle, a driver for forcing the syringe subassembly to penetrate flesh and displace fluid medication through the needle, the driver being movable between a cocked position and extended positions, a driver release for controllably releasing the driver from the cocked position to move toward said extended positions, a removable stop within the barrel for halting movement of the driver at a selected extended position, and a penetration control which can be varied and having an abutment surface which stops movement of the syringe subassembly such that the needle projects from the muzzle end a desired penetration distance, wherein the penetration control comprises a selected compression spring having a predetermined compressed length dimension and having an abutment surface at a rearward end thereof, and further comprising a nose cap releasably mounted to the barrel at the muzzle end.

An apparatus forming a medicine injection device, comprising a barrel having a muzzle end with a needle receiving aperture, a syringe subassembly receiving cavity along the barrel, a syringe subassembly within the barrel and sized to slide within the cavity, the syringe subassembly having an ampule for housing fluid medication, a needle, and a plunger for forcing the fluid medication from the ampule through the needle, a driver for forcing the syringe subassembly to penetrate flesh and displace fluid medication through the needle, the driver being movable between a cocked position and extended positions, a driver release for controllably releasing the driver from the cocked position to move toward said extended positions, a removable stop within the barrel for halting movement of the driver at a selected extended position, and a penetration control which can be varied and having an abutment surface which stops movement of the syringe subassembly such that the needle projects from the muzzle end a desired penetration distance, wherein the penetration control comprises a compression spring having a compressed length dimension and having an abutment surface at a rearward end thereof.

An apparatus forming a medicine injection device comprising a barrel having a muzzle end a syringe subassembly cavity within the barrel, a syringe subassembly within the barrel and sized to slide within the cavity, the syringe subassembly having an ampule for housing fluid medication, a needle, and a plunger for forcing the fluid medication from the ampule through the needle, a driver for forcing the syringe subassembly to penetrate flesh and displace fluid medication through the needle, the driver being movable between a cocked position and extended positions, and a penetration controller comprising a selected coil spring from a series of coil springs of different winding configurations with different compressed axial lengths, the selected coil spring being positioned in the cavity to be engaged and compressed by the syringe subassembly to its contracted axial length in response to movement of the syringe subassembly, to thereby stop movement of the syringe subassembly at a selected stop position with the needle at a selected needle penetration depth.

An apparatus forming a medicine injection device comprising a barrel having a muzzle end a syringe subassembly cavity within the barrel, a syringe subassembly within the barrel and sized to slide within the cavity, the syringe subassembly having an ampule for housing fluid medication, a needle, and a plunger for forcing the fluid medication from the ampule through the needle, a driver for forcing the syringe subassembly to penetrate flesh and displace fluid medication through the needle, the driver being movable between a cocked position and extended positions, and a penetration controller comprising a selected coil spring from a series of coil springs of different winding configurations with different compressed axial lengths, the selected coil spring being positioned in the cavity to be engaged and compressed by the syringe subassembly to its contracted axial length in response to movement of the syringe subassembly, to thereby stop movement of the syringe subassembly at a selected stop position with the needle at a selected needle penetration depth, wherein the muzzle end is selectively covered by a removable nose cap and wherein the selected spring engages the nose cap for removal therewith.

An apparatus forming a medicine injection device comprising a barrel having a muzzle end a syringe subassembly cavity within the barrel, a syringe subassembly within the barrel and sized to slide within the cavity, the syringe subassembly having an ampule for housing fluid medication, a needle, and a plunger for forcing the fluid medication from the ampule through the needle, a driver for forcing the syringe subassembly to penetrate flesh and displace fluid medication through the needle, the driver being movable between a cocked position and extended positions, and a penetration controller comprising a selected coil spring from a series of coil springs of different winding configurations with different compressed axial lengths, the selected coil spring being positioned in the cavity to be engaged and compressed by the syringe subassembly to its contracted axial length in response to movement of the syringe subassembly, to thereby stop movement of the syringe subassembly at a selected stop position with the needle at a selected needle penetration depth, and further comprising a removable nose cap releasably attached to the barrel and abutting an end of the selected spring.

An apparatus forming a medicine injection device comprising a barrel having a muzzle end with a needle receiving aperture, a nose cap which is detachable from said barrel, a syringe subassembly cavity within the barrel, a syringe subassembly within the barrel and sized to slide within said cavity; and a syringe driver to move the syringe subassembly toward the muzzle end through the syringe subassembly cavity; wherein the syringe subassembly can be inserted into the barrel in reverse orientation after an injection has been given and the nose cap and syringe subassembly have been removed to thus serve as a sharps container.

An apparatus forming a medicine injection device comprising a barrel having a muzzle end with a needle receiving aperture, a nose cap which is detachable from said barrel, a syringe subassembly cavity within the barrel, a syringe subassembly within the barrel and sized to slide within said cavity; and a syringe driver to move the syringe subassembly toward the muzzle end through the syringe subassembly cavity; wherein the syringe subassembly can be inserted into the barrel in reverse orientation after an injection has been given and the nose cap and syringe subassembly have been removed to thus serve as a sharps container, and wherein the nose cap is attached to the barrel after insertion of the syringe subassembly in the reverse orientation.

A method for driving a syringe needle to a selected penetration depth comprising locating a syringe subassembly within a barrel having a muzzle end, positioning a penetration control between the muzzle end and syringe subassembly selected from a plurality of penetration controls having different stop positions, and driving the syringe subassembly toward the muzzle end until the syringe subassembly is stopped by the penetration control such that the needle projects a selected penetration depth from said muzzle end.

A method for driving a syringe needle to a selected penetration depth comprising locating a syringe subassembly within a barrel having a muzzle end, positioning a penetration control between the muzzle end and syringe subassembly selected from a plurality of penetration controls having different stop positions, and driving the syringe subassembly toward the muzzle end until the syringe subassembly is stopped by the penetration control such that the needle projects a selected penetration depth from said muzzle end, and wherein positioning the penetration control is accomplished by placing a sleeve of a selected length within the barrel.

A method for driving a syringe needle to a selected penetration depth comprising locating a syringe subassembly within a barrel having a muzzle end, positioning a penetration control between the muzzle end and syringe subassembly selected from a plurality of penetration controls having different stop positions, and driving the syringe subassembly toward the muzzle end until the syringe subassembly is stopped by the penetration control such that the needle projects a selected penetration depth from said muzzle end, and wherein positioning the penetration control is accomplished by placing a compression spring and a sleeve of a selected length within the barrel.

A method for driving a syringe needle to a selected penetration depth comprising locating a syringe subassembly within a barrel having a muzzle end, positioning a penetration control between the muzzle end and syringe subassembly selected from a plurality of penetration controls having different stop positions, and driving the syringe subassembly toward the muzzle end until the syringe subassembly is stopped by the penetration control such that the needle projects a selected penetration depth from said muzzle end, and wherein positioning the penetration control is accomplished by placing at least one compression spring having a selected compressed length dimension within the barrel between the syringe and the muzzle end.

A method for injecting medicine from a syringe and storing the syringe after injection of the medicine comprising providing an injector having a barrel with a syringe therein and a removable nose cap, administering a dose of medicine using said injector, removing the nose cap withdrawing the syringe from the barrel after said nose cap has been removed, and reinserting the syringe back into the barrel in reverse orientation so that the injector serves as a sharps container for the syringe.

A method for injecting medicine from a syringe and storing the syringe after injection of the medicine comprising providing an injector having a barrel with a syringe therein and a removable nose cap, administering a dose of medicine using said injector, removing the nose cap withdrawing the syringe from the barrel after said nose cap has been removed, and reinserting the syringe back into the barrel in reverse orientation so that the injector serves as a sharps container for the syringe, and further comprising reattaching the nose cap to the barrel to lock the syringe therein.

Interpretation Note

The invention has been described in language directed to the current embodiments shown and described with regard to various structural and methodological features. The scope of protection as defined by the claims is not intended to be necessarily limited to the specific features shown and described. Other forms and equivalents for implementing the inventions can be made without departing from the scope of concepts properly protected hereby.

I claim:

1. A method performed during operation of a medicine injection apparatus, comprising:
   selecting a medicine injector having:
      a tube including a barrel and a nose cap attached thereto;
      a receiving cavity within the tube;
      a syringe subassembly within the receiving cavity, the syringe subassembly including a reservoir, an injection needle, a hub between the reservoir and the injection needle, and a resilient cushion on the hub;
      a driver adjacent one end within the tube; and
      a penetration controller adjacent another end within the tube opposite the one end, the penetration controller including a control sleeve that is removable from the tube and a return spring within the control sleeve radially between the control sleeve and a part of the syringe subassembly; the control sleeve having an abutment surface at one end, another end opposite the one end, and an inside diameter; the return spring having an enlarged portion with an outside diameter greater than the inside diameter of the control sleeve; the enlarged portion of the return spring being retained between the other end of the control sleeve and the nose cap; and the resilient cushion being located axially between the abutment surface and at least a part of the hub;
   driving the syringe subassembly toward extension of the injection needle from the barrel, the syringe subassembly contacting the abutment surface;
   absorbing energy of the syringe subassembly and stopping the needle at a desired position using the control sleeve and the return spring; and
   absorbing energy of the syringe subassembly in the resilient cushion.

2. A method according to claim 1 wherein the control sleeve has a length and the spring extends along substantially all of the length of the control sleeve, the spring exhibiting a fully compressed length and the fully compressed length of the spring being less than the length of the control sleeve.

3. A method according to claim 1 wherein the other end of the control sleeve comprises a plurality of flange lobes, the enlarged portion of the spring comprises at least one coil exhibiting the outside diameter, and the at least one coil is retained between the flange lobes and the nose cap.

4. A method according to claim 1 wherein the other end of the control sleeve comprises a plurality of flange lobes, which are in frictional engagement with the nose cap.

5. A method according to claim 1 wherein the resilient cushion is in the form of a ring around the hub.

6. A method according to claim 5 wherein the syringe subassembly further comprises a load distribution ring located axially between the cushion ring and the abutment surface and the absorbing energy in the resilient cushion further comprises the load distribution ring distributing force to the resilient cushion as applied by the syringe subassembly to the abutment surface.

* * * * *

UNITED STATES PATENT AND TRADEMARK OFFICE
CERTIFICATE OF CORRECTION

PATENT NO. : 8,187,224 B2
APPLICATION NO. : 12/569737
DATED : May 29, 2012
INVENTOR(S) : Ronald E. Wyrick It is certified that error appears in the above-identified patent and that said Letters Patent is hereby corrected as shown below:

In the Specifications:

Column 21, line 29 – Replace "type 16 A228" with --type A228--
Column 23, line 63 – Replace "an driver bar" with --a driver bar--
Column 24, line 16 – Replace "an driver bar" with --a driver bar--
Column 24, line 38 – Replace "an driver bar" with --a driver bar--
Column 24, line 61 – Replace "an driver bar" with --a driver bar--
Column 25, line 18 – Replace "an driver bar" with --a driver bar--
Column 25, line 40 – Replace "an driver bar" with --a driver bar--
Column 25, line 63 – Replace "an driver bar" with --a driver bar--
Column 26, line 20 – Replace "an driver bar" with --a driver bar--
Column 26, line 45 – Replace "an driver bar" with --a driver bar--
Column 27, line 2 – Replace "an driver bar" with --a driver bar--
Column 27, line 25 – Replace "an driver bar" with --a driver bar--

Signed and Sealed this
Eighteenth Day of June, 2013

Teresa Stanek Rea
*Acting Director of the United States Patent and Trademark Office*